United States Patent
Altarac et al.

(10) Patent No.: US 10,980,641 B2
(45) Date of Patent: Apr. 20, 2021

(54) INTERBODY SPACER

(71) Applicant: NEUROSTRUCTURES, INC., Irvine, CA (US)

(72) Inventors: Moti Altarac, Irvine, CA (US); Joey Reglos, Lake Forest, CA (US); Babak Barcohana, Los Angeles, CA (US)

(73) Assignee: NeuroStructures, Inc., Irvine, CA (US)

( * ) Notice: Subject to any disclaimer, the term of this patent is extended or adjusted under 35 U.S.C. 154(b) by 106 days.

(21) Appl. No.: 15/587,216

(22) Filed: May 4, 2017

(65) Prior Publication Data
US 2018/0318099 A1 Nov. 8, 2018

(51) Int. Cl.
| A61F 2/44 | (2006.01) |
| A61B 17/80 | (2006.01) |
| A61F 2/30 | (2006.01) |
| A61F 2/46 | (2006.01) |

(52) U.S. Cl.
CPC ........ *A61F 2/4455* (2013.01); *A61B 17/8042* (2013.01); *A61B 17/8033* (2013.01); *A61F 2/4611* (2013.01); *A61F 2002/3082* (2013.01); *A61F 2002/30481* (2013.01); *A61F 2002/30528* (2013.01); *A61F 2002/30593* (2013.01); *A61F 2002/30787* (2013.01); *A61F 2002/30904* (2013.01)

(58) Field of Classification Search
CPC ...... A61F 2/442; A61F 2/4455; A61F 2/4465; A61F 2002/30772; A61F 2002/4475; A61F 2002/30787; A61F 2002/30476; A61F 2002/30528; A61F 2002/3085; A61F 2002/30481; A61B 17/7059; A61B 17/8042; A61B 17/8033; A61B 17/7074; A61B 17/8047

USPC ........ 606/289, 292–293, 295–296, 288, 322, 606/290; 623/17.11–17.16
See application file for complete search history.

(56) References Cited

U.S. PATENT DOCUMENTS

| 3,741,205 A | 6/1973 | Markoff et al. |
| 5,085,660 A | 2/1992 | Lin |
| 5,364,399 A | 11/1994 | Lowery et al. |
| 5,423,826 A | 6/1995 | Coates et al. |

(Continued)

FOREIGN PATENT DOCUMENTS

| EP | 1520545 B1 | 11/2006 |
| EP | 1429675 B1 | 10/2007 |

(Continued)

*Primary Examiner* — Marcela I. Shirsat
(74) *Attorney, Agent, or Firm* — Rimas Lukas

(57) ABSTRACT

An interbody spacer for the spine is provided. The interbody spacer includes a cage and at least one bone screw configured to anchor the cage between two vertebrae of the spine. The cage includes a lock rotationally movable with respect to the cage between a locked configuration and an unlocked configuration. When in an unlocked configuration, bone screws may be inserted and removed from the cage. When in a locked configuration, the insertion and removal pathway of the bone screw is blocked by the lock, thereby, providing backout protection for the bone screws. The lock is coupled to the cage by a pronged retainer and includes a camming surface to provide for incremental rotation of the lock. The lock includes a space-saving shape providing for maximum bone screw angulation on a laterally smaller anterior platform.

14 Claims, 16 Drawing Sheets

(56) References Cited

U.S. PATENT DOCUMENTS

| | | | |
|---|---|---|---|
| 5,549,612 A | 8/1996 | Yapp et al. | |
| 5,616,142 A | 4/1997 | Yuan et al. | |
| 5,616,144 A | 4/1997 | Yapp et al. | |
| 5,676,483 A * | 10/1997 | Koubek | A47C 1/03 |
| | | | 297/411.36 |
| 6,045,552 A | 4/2000 | Zucherman et al. | |
| 6,139,550 A | 10/2000 | Michelson | |
| 6,398,783 B1 | 6/2002 | Michelson | |
| 6,527,776 B1 | 3/2003 | Michelson | |
| 6,599,290 B2 | 7/2003 | Bailey et al. | |
| 6,602,255 B1 | 8/2003 | Campbell et al. | |
| 6,626,907 B2 | 9/2003 | Campbell et al. | |
| 6,652,525 B1 | 11/2003 | Assaker et al. | |
| 6,695,846 B2 | 2/2004 | Richelsoph et al. | |
| 6,849,093 B2 * | 2/2005 | Michelson | A61F 2/446 |
| | | | 623/17.11 |
| 6,926,718 B1 | 8/2005 | Michelson | |
| 6,936,051 B2 | 8/2005 | Michelson | |
| 6,964,664 B2 | 11/2005 | Fried et al. | |
| 7,175,623 B2 | 2/2007 | Thramann et al. | |
| 7,186,254 B2 | 3/2007 | Dinh et al. | |
| 7,220,263 B2 | 5/2007 | Cordaro | |
| 7,273,481 B2 | 9/2007 | Lombardo et al. | |
| 7,276,070 B2 | 10/2007 | Muckter | |
| 7,278,997 B1 | 10/2007 | Mueller et al. | |
| 7,288,094 B2 | 10/2007 | Lindemann et al. | |
| 7,288,095 B2 | 10/2007 | Baynham et al. | |
| 7,291,152 B2 | 11/2007 | Abdou | |
| 7,306,605 B2 | 12/2007 | Ross | |
| 7,318,825 B2 | 1/2008 | Butler et al. | |
| 7,524,325 B2 | 4/2009 | Khalili | |
| 7,601,170 B2 | 10/2009 | Winslow et al. | |
| 7,651,517 B2 | 1/2010 | Konieczynski et al. | |
| 7,662,154 B2 | 2/2010 | Ribeiro | |
| 7,686,806 B2 | 3/2010 | Rhyne | |
| 7,704,255 B2 | 4/2010 | Michelson | |
| 7,740,630 B2 | 6/2010 | Michelson | |
| 7,803,157 B2 | 9/2010 | Michelson | |
| 7,811,285 B2 | 10/2010 | Michelson | |
| 7,815,666 B2 | 10/2010 | Baynham et al. | |
| 7,824,432 B2 | 11/2010 | Michelson | |
| 7,887,547 B2 | 2/2011 | Campbell et al. | |
| 8,048,075 B2 | 11/2011 | Michelson | |
| 8,206,293 B2 | 6/2012 | Reglos et al. | |
| 8,439,924 B1 | 5/2013 | McBride et al. | |
| 8,460,308 B2 | 6/2013 | Marino et al. | |
| 8,652,182 B1 | 2/2014 | Walker et al. | |
| 8,668,723 B2 | 3/2014 | Altarac et al. | |
| 9,326,861 B2 * | 5/2016 | Iott | A61F 2/442 |
| 9,381,093 B1 * | 7/2016 | Morris | A61B 17/7059 |
| 9,743,958 B2 | 8/2017 | Ishii et al. | |
| 10,016,224 B2 | 7/2018 | Altarac et al. | |
| 2002/0120270 A1 | 8/2002 | Trieu et al. | |
| 2003/0060828 A1 | 3/2003 | Michelson | |
| 2003/0093082 A1 | 5/2003 | Campbell et al. | |
| 2003/0105462 A1 | 6/2003 | Haider | |
| 2003/0105466 A1 | 6/2003 | Ralph et al. | |
| 2003/0105467 A1 | 6/2003 | Ralph et al. | |
| 2003/0125739 A1 | 7/2003 | Bagga et al. | |
| 2003/0135216 A1 | 7/2003 | Sevrain | |
| 2003/0153920 A1 | 8/2003 | Ralph et al. | |
| 2003/0171753 A1 | 9/2003 | Collins et al. | |
| 2003/0181912 A1 | 9/2003 | Michelson | |
| 2003/0187440 A1 | 10/2003 | Richelsoph et al. | |
| 2003/0187442 A1 | 10/2003 | Richelsoph et al. | |
| 2003/0187509 A1 | 10/2003 | Lemole, Jr. | |
| 2003/0191471 A1 | 10/2003 | Michelson | |
| 2003/0191472 A1 | 10/2003 | Michelson | |
| 2003/0208204 A1 | 11/2003 | Bailey et al. | |
| 2003/0229348 A1 | 12/2003 | Sevrain | |
| 2003/0236528 A1 | 12/2003 | Thramann | |
| 2004/0006343 A1 | 1/2004 | Sevrain | |
| 2004/0015169 A1 | 1/2004 | Gause | |
| 2004/0019353 A1 | 1/2004 | Freid et al. | |
| 2004/0024081 A1 | 2/2004 | Trieu et al. | |
| 2004/0030336 A1 | 2/2004 | Khanna | |
| 2004/0034352 A1 | 2/2004 | Needham et al. | |
| 2004/0039387 A1 | 2/2004 | Gause et al. | |
| 2004/0049279 A1 | 3/2004 | Sevrain | |
| 2004/0068319 A1 | 4/2004 | Cordaro | |
| 2004/0087945 A1 | 5/2004 | Ralph et al. | |
| 2004/0087951 A1 | 5/2004 | Khalili | |
| 2004/0092929 A1 | 5/2004 | Zindrick | |
| 2004/0092947 A1 | 5/2004 | Foley | |
| 2004/0097925 A1 | 5/2004 | Boehm, Jr. et al. | |
| 2004/0097934 A1 | 5/2004 | Farris et al. | |
| 2004/0097935 A1 | 5/2004 | Richelsoph et al. | |
| 2004/0097938 A1 | 5/2004 | Alleyne | |
| 2004/0097950 A1 | 5/2004 | Foley et al. | |
| 2004/0106924 A1 | 6/2004 | Ralph et al. | |
| 2004/0122426 A1 | 6/2004 | Michelson | |
| 2004/0127897 A1 | 7/2004 | Freid et al. | |
| 2004/0127899 A1 | 7/2004 | Konieczynski et al. | |
| 2004/0127900 A1 | 7/2004 | Konieczynski et al. | |
| 2004/0133205 A1 | 7/2004 | Thramann et al. | |
| 2004/0153088 A1 | 8/2004 | Ralph et al. | |
| 2004/0158246 A1 | 8/2004 | Assaker et al. | |
| 2004/0177847 A1 | 9/2004 | Foley et al. | |
| 2004/0181226 A1 | 9/2004 | Michelson | |
| 2004/0181229 A1 | 9/2004 | Michelson | |
| 2004/0186476 A1 | 9/2004 | Michelson | |
| 2004/0204710 A1 | 10/2004 | Patel et al. | |
| 2004/0204712 A1 | 10/2004 | Kolb et al. | |
| 2004/0204713 A1 | 10/2004 | Abdou | |
| 2004/0210314 A1 | 10/2004 | Michelson | |
| 2004/0215192 A1 | 10/2004 | Justis et al. | |
| 2004/0215195 A1 | 10/2004 | Shipp et al. | |
| 2004/0220571 A1 | 11/2004 | Assaker et al. | |
| 2004/0220572 A1 | 11/2004 | Michelson | |
| 2004/0225290 A1 | 11/2004 | Ferree | |
| 2004/0236333 A1 | 11/2004 | Lin | |
| 2004/0236334 A1 | 11/2004 | Michelson | |
| 2004/0236335 A1 | 11/2004 | Michelson | |
| 2004/0243128 A1 | 12/2004 | Howland | |
| 2004/0260306 A1 | 12/2004 | Fallin et al. | |
| 2005/0015092 A1 | 1/2005 | Rathbun et al. | |
| 2005/0015093 A1 | 1/2005 | Suh et al. | |
| 2005/0027296 A1 | 2/2005 | Thramann et al. | |
| 2005/0027297 A1 | 2/2005 | Michelson | |
| 2005/0027298 A1 | 2/2005 | Michelson | |
| 2005/0033298 A1 | 2/2005 | Hawkes et al. | |
| 2005/0038436 A1 | 2/2005 | Michelson | |
| 2005/0043732 A1 | 2/2005 | Dalton | |
| 2005/0059970 A1 | 3/2005 | Kolb | |
| 2005/0059971 A1 | 3/2005 | Michelson | |
| 2005/0075633 A1 | 4/2005 | Ross | |
| 2005/0085816 A1 | 4/2005 | Michelson | |
| 2005/0137597 A1 | 6/2005 | Butler et al. | |
| 2005/0149021 A1 | 7/2005 | Tozzi | |
| 2005/0149026 A1 | 7/2005 | Butler et al. | |
| 2005/0149027 A1 | 7/2005 | Campbell et al. | |
| 2005/0171551 A1 | 8/2005 | Sukovich et al. | |
| 2005/0177160 A1 | 8/2005 | Baynham et al. | |
| 2005/0177161 A1 | 8/2005 | Baynham et al. | |
| 2005/0177163 A1 | 8/2005 | Abdou | |
| 2005/0187552 A1 | 8/2005 | Michelson | |
| 2005/0187553 A1 | 8/2005 | Grabowski et al. | |
| 2005/0187554 A1 | 8/2005 | Michelson | |
| 2005/0192576 A1 | 9/2005 | Michelson | |
| 2005/0208095 A1 | 9/2005 | Hunter et al. | |
| 2005/0209593 A1 | 9/2005 | Kolb | |
| 2005/0216005 A1 | 9/2005 | Howland | |
| 2005/0216009 A1 | 9/2005 | Michelson | |
| 2005/0216010 A1 | 9/2005 | Michelson | |
| 2005/0228386 A1 | 10/2005 | Ziolo et al. | |
| 2005/0234455 A1 | 10/2005 | Binder et al. | |
| 2005/0261690 A1 | 11/2005 | Binder et al. | |
| 2005/0273105 A1 | 12/2005 | Konieczynski et al. | |
| 2005/0277930 A1 | 12/2005 | Parsons | |
| 2005/0277938 A1 | 12/2005 | Parsons | |
| 2006/0009845 A1 | 1/2006 | Chin | |
| 2006/0030852 A1 | 2/2006 | Sevrain | |
| 2006/0079961 A1 | 4/2006 | Michelson | |
| 2006/0082015 A1 | 4/2006 | Happonen et al. | |

(56) References Cited

U.S. PATENT DOCUMENTS

| | | |
|---|---|---|
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200146 A1 | 9/2006 | Doubler et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |
| 2006/0276792 A1 | 12/2006 | Ensign et al. |
| 2006/0287653 A1 | 12/2006 | Rhyne |
| 2007/0083203 A1 | 4/2007 | Ribeiro |
| 2007/0123884 A1 | 5/2007 | Abdou |
| 2007/0167954 A1 | 7/2007 | Sicvol et al. |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |
| 2007/0233110 A1 | 10/2007 | Muhanna et al. |
| 2007/0233117 A1 | 10/2007 | Butler et al. |
| 2007/0233118 A1 | 10/2007 | McLain |
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0051794 A1 | 2/2008 | Dec et al. |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0269806 A1 | 10/2008 | Zhang et al. |
| 2008/0287999 A1 | 11/2008 | Markworth |
| 2008/0288001 A1 | 11/2008 | Cawley et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1 | 7/2009 | Sanders et al. |
| 2009/0210008 A1 | 8/2009 | Butler et al. |
| 2009/0222049 A1 | 9/2009 | Frigg et al. |
| 2009/0259226 A1 | 10/2009 | Michelson |
| 2009/0270926 A1 | 10/2009 | Hawkes |
| 2010/0016901 A1 | 1/2010 | Robinson |
| 2010/0042159 A1 | 2/2010 | Butler |
| 2010/0049256 A1 | 2/2010 | Jeon et al. |
| 2010/0057206 A1* | 3/2010 | Duffield ............... A61F 2/442 623/17.16 |
| 2010/0069968 A1 | 3/2010 | Assaker et al. |
| 2010/0145459 A1* | 6/2010 | McDonough ...... A61B 17/1728 623/17.16 |
| 2010/0234897 A1 | 9/2010 | Fisher et al. |
| 2010/0312279 A1 | 12/2010 | Gephart et al. |
| 2011/0054528 A1 | 3/2011 | Michelson |
| 2011/0106159 A1 | 5/2011 | Nazeck |
| 2011/0118784 A1 | 5/2011 | Baynham et al. |
| 2011/0190770 A1 | 8/2011 | Suh |
| 2011/0230885 A1 | 9/2011 | Weiner et al. |
| 2011/0313477 A1 | 12/2011 | McLean et al. |
| 2012/0109208 A1 | 5/2012 | Justis et al. |
| 2012/0245690 A1 | 9/2012 | Cowan, Jr. et al. |
| 2013/0023936 A1 | 1/2013 | Altarac et al. |
| 2013/0046345 A1 | 2/2013 | Jones et al. |
| 2013/0060294 A1 | 3/2013 | Donahue |
| 2013/0245705 A1 | 9/2013 | McBride et al. |
| 2013/0261679 A1 | 10/2013 | McBride et al. |
| 2013/0331892 A1 | 12/2013 | Peterson et al. |
| 2014/0142632 A1 | 5/2014 | Keyer et al. |
| 2014/0148860 A1 | 5/2014 | Rinner |
| 2014/0277145 A1 | 9/2014 | Reiblat et al. |
| 2014/0277206 A1 | 9/2014 | Reitblat et al. |
| 2015/0039035 A1 | 2/2015 | Kruger |
| 2015/0094772 A1* | 4/2015 | Black ............... A61B 17/8033 606/290 |
| 2016/0022317 A1 | 1/2016 | Kraus |
| 2016/0128746 A1* | 5/2016 | Dunaway ........... A61B 17/8042 606/246 |

FOREIGN PATENT DOCUMENTS

| | | |
|---|---|---|
| EP | 1841376 A2 | 10/2007 |
| EP | 1847229 A2 | 10/2007 |
| WO | WO2006076422 A2 | 7/2006 |
| WO | WO2007037774 A1 | 4/2007 |
| WO | WO2007101266 A1 | 9/2007 |
| WO | WO2007103081 A2 | 9/2007 |
| WO | WO2007121080 A2 | 10/2007 |
| WO | WO2006138291 B1 | 11/2007 |
| WO | WO2007134199 A2 | 11/2007 |
| WO | WO2009089395 A2 | 7/2009 |
| WO | WO2009091770 A1 | 7/2009 |
| WO | WO2009091775 A2 | 7/2009 |

* cited by examiner

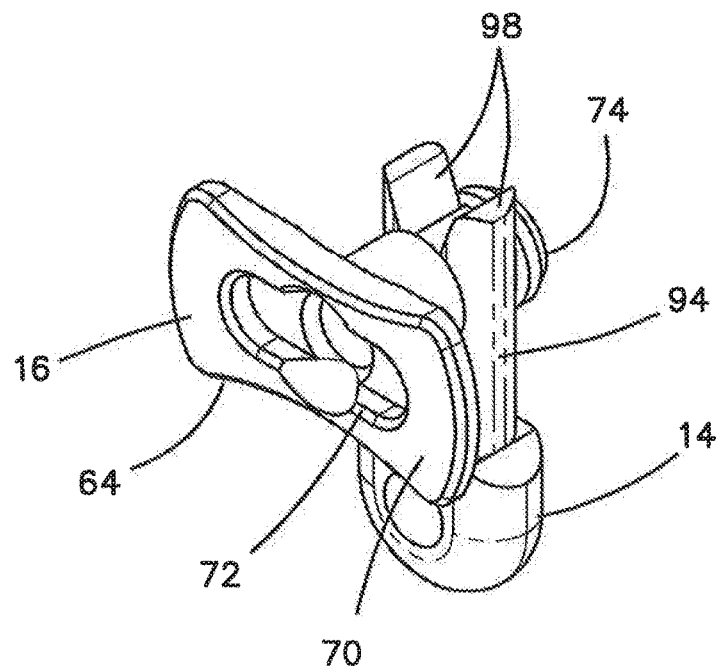
FIG. 28
FIG. 29
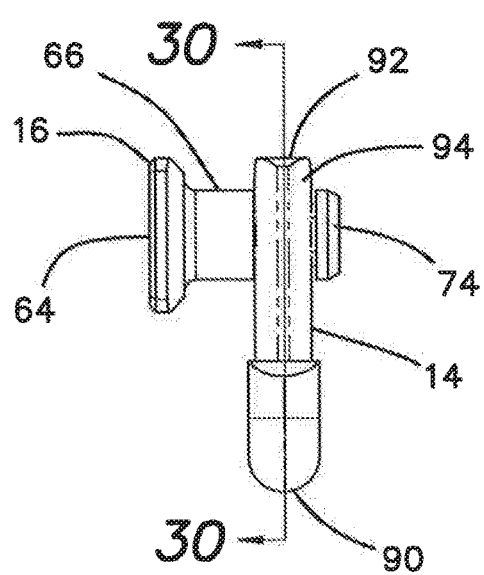
FIG. 30
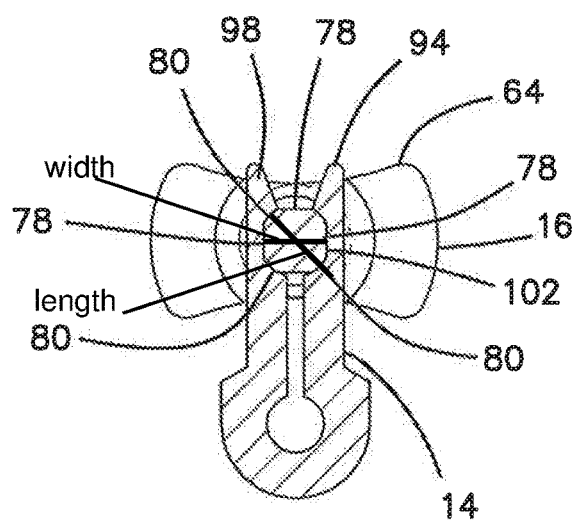

INTERBODY SPACER

FIELD OF THE INVENTION

This application relates generally to spinal implants, and in particular, intervertebral spacers and fusion cages.

BACKGROUND OF THE INVENTION

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In a posterior lumbar interbody fusion (PLIF) surgery, spinal fusion is achieved in the lower back by inserting an implant such as a cage and typically graft material to encourage bone ingrowth directly into the disc space between adjacent vertebrae. The surgical approach for PLIF is from the back of the patient, posterior to the spinal column. An anterior lumbar interbody fusion (ALIF) surgical procedure is similar to the PLIF procedure except that in the ALIF procedure, the disc space is fused by approaching the spine through the abdomen from an anterior approach instead of from a posterior approach. Another fusion procedure is called a transforaminal lumbar interbody fusion (TLIF) which involves a posterior and lateral approach to the disc space. To gain access to the disc space, the facet joint may be removed whereby access is gained via the nerve foramen. In an extreme lateral interbody fusion (XLIF), the disc space is accessed from small incisions on the patient's side.

In the typical procedures described above, the adjacent vertebrae must be distracted apart by a substantial amount in order to allow the surgeon to advance the implant with relatively little resistance along the delivery path. Also, the surgeon must typically release the implant at least once as the implant is being delivered along the delivery path and align and position the implant at the target position of implantation, typically in the anterior aspect of the disc space. Once positioned, the interbody spacer is secured to the adjacent vertebrae with one or more bone screws. The implant includes apertures formed at one end for passing one or more bone screws at an upward angle into the first adjacent vertebral body and one or more bone screws at a downward angle into the second adjacent vertebral body.

Over time, the interface between the screws and the bone may present some problems of stability. Due to the anatomical structure of the spine and the extreme anatomical forces that are brought to bear on the skeleton and transmitted to the vertebral bodies, the screws securing the interbody spacer to the spine may vibrate or toggle out of position. Also, the degeneration of vertebral bone quality may result in the screws loosening or becoming dislodged. As a result, bone screws may move or back out of the vertebral body and implant. Loosened screws may result instability of the joint and lead to increased pain for the patient.

Therefore, there is a need to provide a new and improved interbody spacer that resists fasteners, such as bone screws, from backing out and also from being loosened with respect to the implant before migrating out. Furthermore, there is a need for the implant to withstand anatomical forces and be easily implanted. Also, the screw retaining mechanism must be easily activated by the surgeon. This invention, as described in the detailed description, sets forth an improved interbody spacer that meets these needs.

SUMMARY OF THE INVENTION

According to one aspect of the invention, an interbody spacer for the spine is provided. The interbody spacer includes a cage having a top surface and a bottom surface interconnected by a sidewall. The cage includes a central opening extending between the top surface and the bottom surface and defining an inner surface. The cage includes at least one bone screw aperture in the sidewall. The cage includes a lock aperture that is sized and configured to receive a lock. At least one bone screw is disposed inside the at least one bone screw aperture. Each bone screw has a head at a proximal end and a threaded shank extending toward a distal end for anchoring into bone. The bone screw is configured to secure the interbody spacer between two bony components of the spine. The interbody spacer further includes a lock connected to the cage and located inside the lock aperture. The lock has an unlocked position in which the lock does not cover the head of the bone screw inside the bone screw aperture permitting passage of the bone screw in or out of the bone screw aperture and a locked position in which at least part of the lock is above the head of the bone screw to prevent the bone screw from backing out of the bone screw aperture. Rotation of the lock moves the lock between the unlocked position and the locked position.

According to another aspect of the invention, an interbody spacer for the spine is provided. The interbody spacer includes a cage having a top surface and a bottom surface interconnected by a sidewall. The cage includes a central opening extending between the top surface and the bottom surface defining an inner surface and a longitudinal axis. The cage includes at least one bone screw aperture in the sidewall. The cage includes a lock aperture that is sized and configured to receive a lock. At least one bone screw is disposed inside the at least one bone screw aperture. Each bone screw has a head at a proximal end and a threaded shank extending toward a distal end for anchoring into bone. The at least one bone screw is configured to secure the interbody spacer between two bony components of the spine. The interbody spacer includes a lock connected to the cage such that the lock is capable of rotational movement with respect to the cage. The lock includes a main body connected to a post. The post is located inside the lock aperture. The lock includes an unlocked position in which the main body does not cover the head of the bone screw inside the bone screw aperture permitting passage of the bone screw in or out of the bone screw aperture and a locked position in which at least part of the main body is above the head of the bone screw to prevent the bone screw from backing out of the bone screw aperture. Rotation of the lock moves the lock between the unlocked position and the locked position. The main body has a cross-section taken perpendicular to the longitudinal axis of the lock. The cross-section has a length and a width. The length is longer than the width. The main body has two oppositely disposed sides along the length interconnected by two oppositely disposed ends along the width. When in the unlocked position, the length is orientated along the longitudinal axis of the cage. At least one of the two sides is curved inwardly to create a concave side facing the at least one bone screw aperture.

BRIEF DESCRIPTION OF THE DRAWINGS

FIG. 28 is a top perspective view of a retainer and lock in a locked configuration according to the present invention.

FIG. 29 is a side view of a retainer and lock in a locked configuration according to the present invention.

FIG. 30 is a cross-sectional view taken along line 30-30 of FIG. 29 of a retainer and lock in a locked configuration according to the present invention.

DETAILED DESCRIPTION OF THE INVENTION

Figure 1:
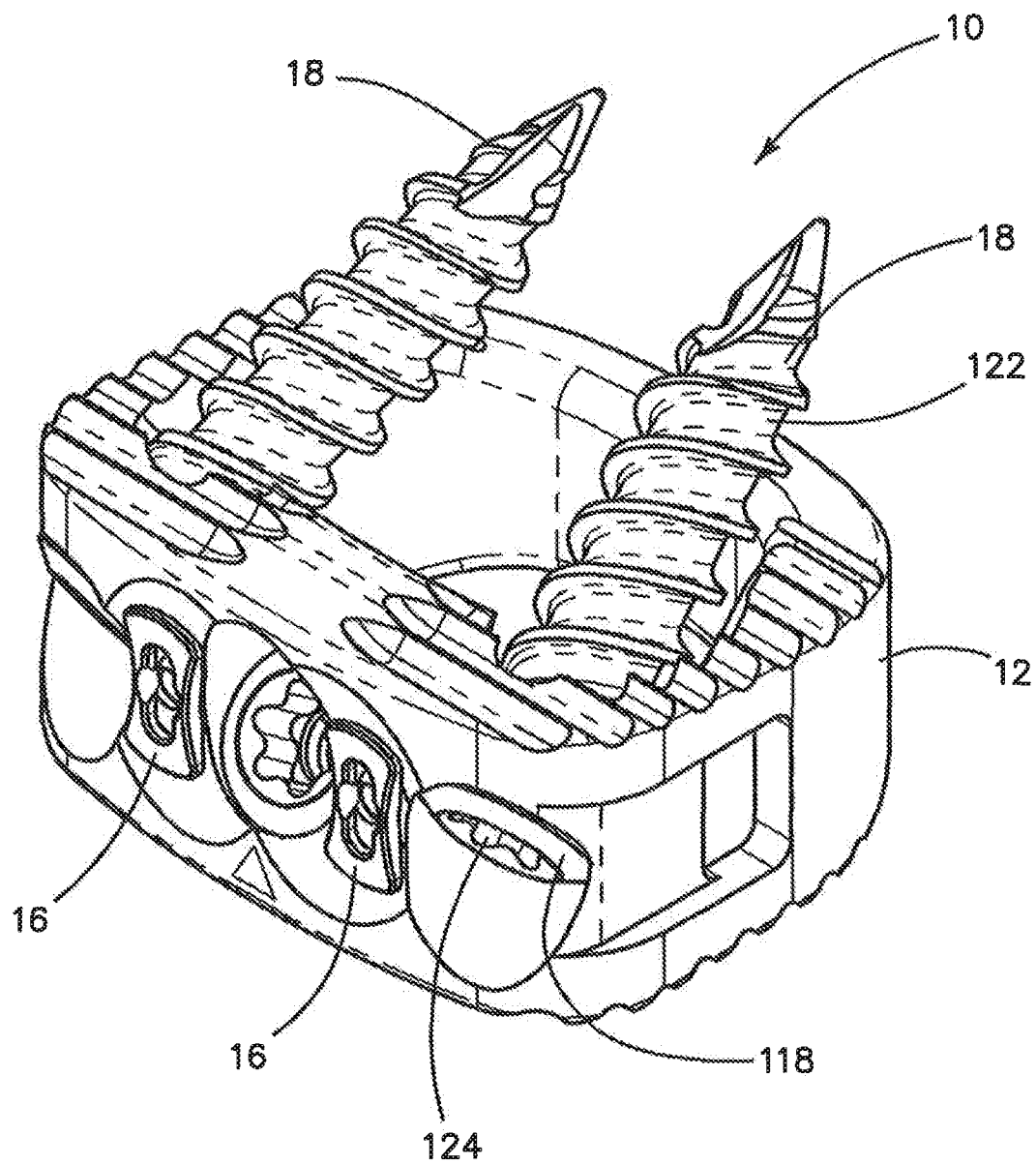
FIG. 1 is a top perspective view of an interbody spacer in an unlocked configuration according to the present invention.

FIGS. 1-10 depict an interbody spacer 10 according to one variation of the invention that may be used to stabilize or fuse vertebral bodies in the lumbar or other region of the spine. The interbody spacer 10 comprises a cage 12, at least one lock retainer 14, at least one lock 16, and bone screws 18. The figures depict an interbody spacer 10 having three bone screws 18, two locks 16 and two lock retainers 14 that correspond to the two locks 16. The lock retainers 14 are connected to the cage 12. Each lock retainer 14 is configured to receive a portion of a lock 16 and capture the lock 16 in order to connect the lock 16 to the cage 12 in a manner that permits rotational movement of the lock 16 about its longitudinal axis relative to the cage 12. Bone screws 18 are inserted into the cage 12 and when positioned into bone, each lock 16 is rotated from an unlocked configuration in which each lock 16 does not cover the one or more bone screw 18 to a locked configuration in which each lock 16 covers the one or more bone screw 18. In the locked configuration, the at least one lock 16 prevents the backing out of the at least one bone screw 18 with respect to the cage 12. The figures illustrate each lock 16 covering two bone screws 18 when in the locked configuration. The middle bone screw 18 is covered by two locks 16. The figures show two locks 16 covering three bone screws 18; however, the invention is not so limited and other arrangements of locks 16 and bone screws 18 are within the spirit and scope of the present invention. For example, three locks 16 may be employed to cover three bone screws 18. The bone screws 18 are configured relative to the cage 12 to anchor the interbody spacer 10 between two bony components of the spine. Optional radiographic markers are embedded within the cage 12.

Figure 14:
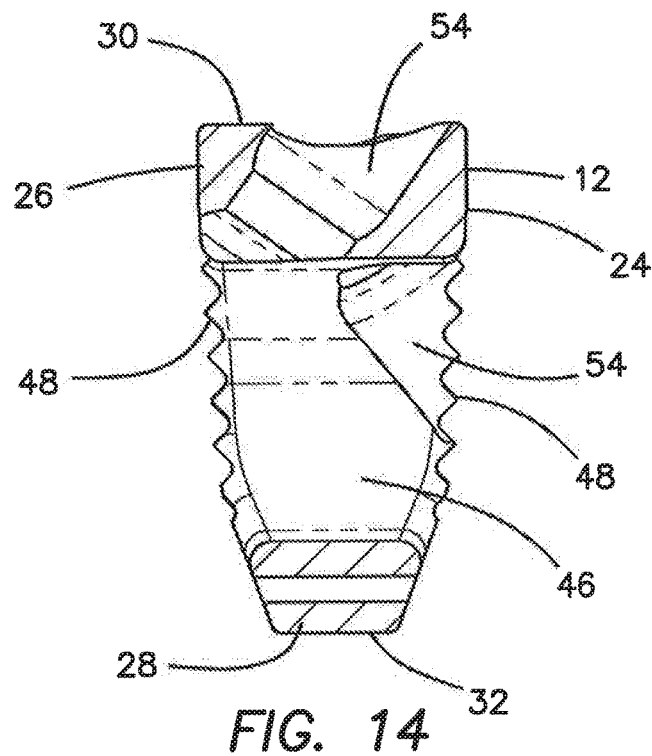
FIG. 14 is a cross-sectional view taken along line 14-14 of FIG. 13 of a cage according to the present invention.
Figure 31:
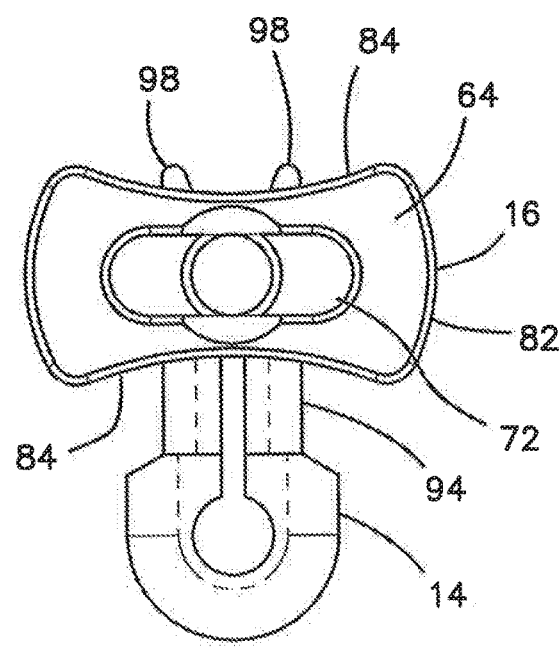
FIG. 31 is a front elevational view of a retainer and lock in a locked configuration according to the present invention.
Figure 32:
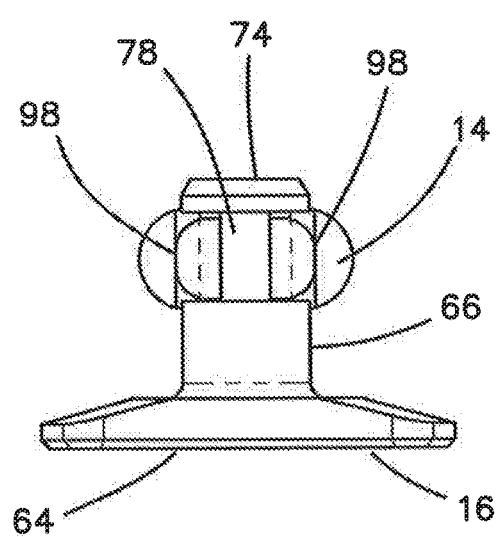
FIG. 32 is a top planar view of a retainer and lock in a locked configuration according to the present invention.
Figure 16:
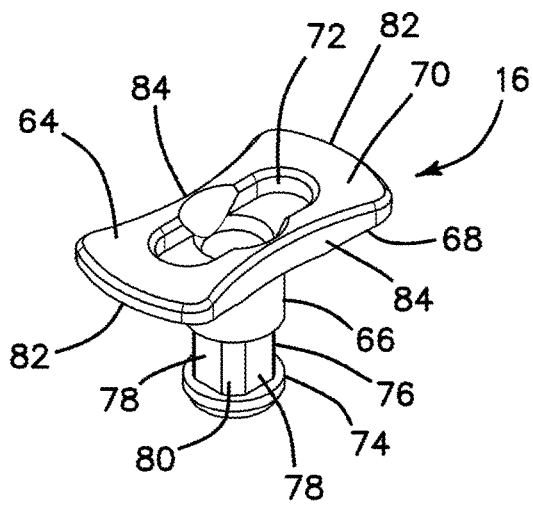
FIG. 16 is a top perspective view of a lock according to the present invention.
Figure 17:
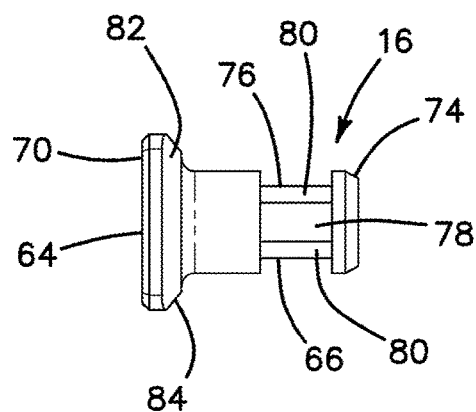
FIG. 17 is a side view of a lock according to the present invention.
Figure 18:
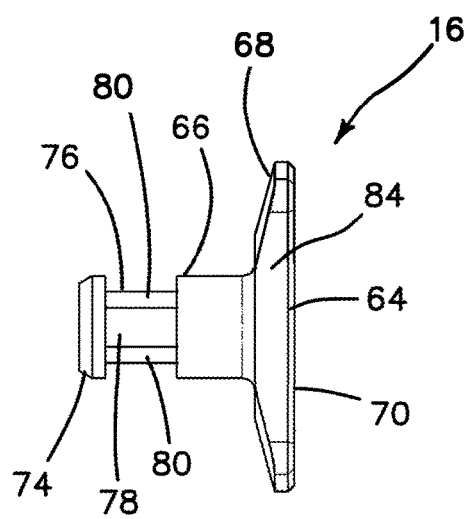
FIG. 18 is a side view of a lock according to the present invention.
Figure 19:
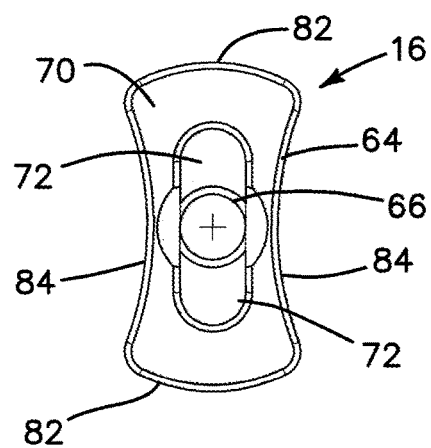
FIG. 19 is a top planar view of a lock according to the present invention.
Figure 20:
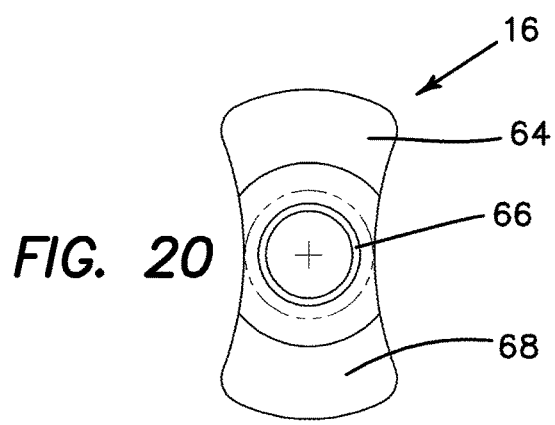
FIG. 20 is a bottom planar view of a lock according to the present invention.

Turning now to the FIGS. 11-15, the cage 12 will now be described in greater detail. The cage 12 includes a top surface 24 and a bottom surface 26 interconnected by at least one sidewall 28 extending between the top surface 24 and the bottom surface 26 defining a cage height. The cage 12 has a shape that mimics a spinal disc. The sidewall 28 has an anterior surface 30 and a posterior surface 32 interconnected by two side surfaces 34, 36. The anterior surface 30 has a larger cage height relative to the posterior surface 32 imparting the cage 12 with a wedge-like configuration having a taper from the anterior surface 30 to the posterior surface 32 as can be seen in FIG. 14. This taper is designed to accommodate the natural anatomic relationship between adjacent vertebral bones and maintain the normal lordotic curvature of the spine. The cage 12 has a lordotic angle that is between approximately 5 degrees and 15 degrees. The lordotic angle can be between approximately 5 degrees and 28 degrees. The cage 12 has a cage height of approximately 10-20 mm such as approximately 12 mm, 14 mm, 16 mm and 18 mm. The anterior and posterior surfaces 30, 32 are longer than the side surfaces 34, 36 when measured along a lateral dimension giving the cage 12 an elongate shape when viewed along the longitudinal axis. The lateral dimension of the cage 12 as measured between side surfaces 34, 36 is approximately 25 mm-40 mm and the anterior-to-posterior dimension is approximately 20 mm-30 mm. The intersections of the surfaces 30, 32, 34 and 36 are smooth and rounded giving the cage 12 an overall oval or oblong shape.

The anterior surface 30 of the cage 12 includes a lock recess 38. The lock recess 38 is sized and configured to conform and to receive the at least one lock 16. When the at least one lock 16 is attached to the cage 12, the lock 16 is recessed such that the lock 16 does not significantly protrude or extend outwardly from the anterior surface 30. In one variation, the depth of the lock recess 38 substantially equals the thickness of the head of the lock 16 such that the lock 16 is flush with the anterior surface 30 when attached to the cage 12. The cage 12 further includes a lock aperture 40 having a longitudinal axis. In one variation, the lock aperture 40 is formed in the anterior surface 30 of the cage 12 such that the longitudinal axis of the lock aperture 40 is substantially perpendicular. In one variation, the lock aperture 40 is located within the perimeter of a lock recess 38. In one variation, the cage 12 does not include any lock recesses 38. In such a variation, the lock aperture 40 may be sized and shaped to recess the lock 16 when it is in the locked configuration. The lock aperture 40 is sized and configured to receive at least a portion of the lock 16. One or more lock recesses 38 may be formed to accommodate the one or more locks 16. Also, a single lock recess 38 may be large enough to accommodate more than one lock aperture 40 and lock 16 received therein. As shown in the figures two lock apertures 40 are formed to accommodate two or more locks 16 received therein. One or more lock recesses may be formed to accommodate the locks 16 and their position on the cage 12.

The side surfaces 34, 36 of the cage 12 each include instrument notches 42 which serve as tool receiving recesses that are sized and configured to receive oppositely disposed distal prongs of an insertion instrument used for delivering, implanting and removing the interbody spacer 10. The instrument notches 42 are formed laterally oppositely from each other near the lateral axis of the cage 12. The instrument notches 42 may include a ramped surface such that the prongs of an insertion instrument do not unduly extend laterally outwardly from the side surfaces 34, 36.

The top surface 24 or superior surface of the cage 12 is configured for engaging a lower endplate of a first vertebral bone and the bottom surface 26 or inferior surface of the cage 12 is configured for engaging an upper endplate of an adjacent second vertebral bone of the spine. The top and bottom surfaces 24, 26 are spaced apart with the sidewall 28 extending therebetween. The top and bottom surfaces 24, 26 define a longitudinal axis extending substantially normal to the top and bottom surfaces 24, 26. It is understood that the longitudinal axis is not precisely normal to the top and bottom surfaces 24, 26 due to the narrowing height and lordotic angle of the cage 12 from the anterior surface 30 to the posterior surface 32. The longitudinal axis of the cage 12 is approximately parallel to or substantially coaxial with the longitudinal direction of the spine when the interbody spacer 10 is implanted. Extending between the top surface 24 and the bottom surface 26 is a central cage opening 44 having an opening at the top surface 24 and extending to an opening at the bottom surface 26 and, thereby, defining an inner surface 46 and central lumen of the cage 12. The central cage opening 44 reduces the weight of the cage 12 and permits bone ingrowth to take place into and through the cage 12. A family of bone graft materials, such as autograft, bone morphogenic protein (BMP), bone marrow aspirate, concentrate, stem cells and the like, may be placed inside the central cage opening 44 to promote bone growth into the cage 12. A plurality of ridges 48 are formed on the top surface 24 and the bottom surface 26. The ridges 48 have pointed peaks to engage and increase the purchase on the endplates of adjacent vertebra. The ridges 48 may further be angled with respect to the top and bottom surfaces 24, 26 such that the ridges 48 help to hold and prevent migration of the cage 12 relative to the adjacent vertebrae when implanted within the intervertebral space.

The bottom surface 26 of the cage 12 includes at least one retainer opening 50 extending from the bottom surface 26 toward the top surface 24. Alternatively, the at least one retainer opening 50 is formed in the top surface 24 extending from the top surface 24 toward the bottom surface 26. The figures illustrate two retainer openings 50 sized and configured to receive two lock retainers 14 therein, formed in the bottom surface 26 and extending toward the top surface 24 of the cage 12. The number of retainer openings 50 in the cage 12 corresponds to the number of lock retainers 14 employed which in turn corresponds to the number of locks 16 used. Also, the retainer openings 50 may be formed in both the top surface 24 and the bottom surface 26 as well as in the side surfaces 34, 36. The retainer opening 50 is sized and configured to receive a lock retainer 14. The figures illustrate the retainer opening 50 having a larger proximal end and a smaller distal end to conform to the size and shape of a corresponding lock retainer 14 that is inserted therein. The top surface 24 and/or the bottom surface 26 of the cage 12 may include one or more radiographic pin holes for receiving radiographic markers. In the figures, the longitudinal axis of the retainer opening 50 is substantially perpendicular to the bottom surface 26. Generally, the retainer opening 50 is substantially perpendicular to the lock aperture 40 and intersects therewith.

The cage 12 further includes one or more bone screw apertures 54 formed in the sidewall 28 configured to direct bone screws 18 upwardly and/or downwardly to engage adjacent vertebrae. In the variation shown in the figures, two bone screw apertures 54 are formed in the anterior surface 30 intersecting with the at least one lock recess 38 and extend transversely across the sidewall 28 and open into the inner surface 46 and top surface 24 of the cage 12. One or more bone screw apertures 54 are angled toward the top surface 24 such that bone screws 18 inserted therein are directed into the lower endplate of the adjacent upper vertebra. Two bone screw apertures 54 are shown angled upwardly toward the upper vertebral body. One or more bone screw apertures 54 are angled toward the bottom surface 26 such that bone screws 18 inserted therein are directed into the upper endplate of the adjacent lower vertebra. One bone screw aperture 54 is formed in the anterior surface 30 intersecting with the at least one lock recess 38 and extends transversely across the sidewall 28 and opens into the inner surface 46 and bottom surface 26 of the cage 12. One bone screw aperture 54 is shown angled downwardly toward the lower vertebral body. Each bone screw aperture 54 may include an interior ledge for contact with the head of the bone screw 18. The interior ledge divides the bone screw aperture 54 into a bone screw shaft receiving portion and a bone screw head receiving portion. The inner diameter of the head receiving portion is larger than the inner diameter of the shaft receiving portion to accommodate the relatively larger head of the bone screw 18 and to permit it to angulate substantially polyaxially. The angulation of the bone screw aperture 54 results in a fluted entry best seen in the figures. All of the bone screw apertures 54 are formed near lock apertures 40 such that when a lock 16 is installed and rotated into a locked configuration, it covers at least one of the bone screws 18 inserted therein to prevent it from backing out of the cage 12. The bone screw aperture 54 that is angled downwardly is formed between two bone screw apertures 54 that are angled upwardly and substantially along the midline of the cage 12. A lock aperture 40 is located between two bone screw apertures 54.

Turning now to FIGS. 16-20, the lock 16 will now be described in greater detail. The lock 16 includes a main body 64 connected to a post 66. The post 66 extends from the bottom surface 68 of the main body 64 along the longitudinal axis of the lock 16. The post 66 is configured to be inserted into the lock aperture 40 of the cage 12 and connected to the cage 12 via the lock retainer 14 such that the lock 16 can rotate relative to the cage 12 about the longitudinal axis of the post 66. Whereas the post 66 is inserted into the cage 12, the main body 64 of the lock 16 resides above the sidewall 28 of the cage 12 next to at least one bone screw aperture 54 in the location of a lock recess 38 if a lock recess 38 is provided preferably such that the main body 64 of the lock 16 does not substantially extend beyond the outer profile of the cage 12 maintaining an anterior surface 30 having a smooth low profile.

The main body 64 includes a bottom surface 68 and a top surface 70. The top surface 70 includes a socket 72. The socket 72 is configured to receive an instrument such as a driver having a complementary shaped tip for engaging and rotating the lock 16 between an unlocked position and a locked position. The lock post 66 extends downwardly from the bottom surface 68 of the main body 64. The lock post 66 includes a distal stop 74 and neck 76. The neck 76 is proximal to the distal stop 74 and has a perimeter diameter that is smaller than the diameter of the distal stop 74. The distal stop 74 extends radially outwardly from the longitudinal axis of the lock 16 relative to the neck 76 and circumferentially around the lock post 66. The neck 76 is faceted and, in a cross-section perpendicular to the longitudinal axis, has a polygonal shape that can be described as having two oppositely disposed parallel sides 78 that are interconnected to two oppositely disposed parallel sides 78 by beveled corners 80 for a total of eight facets that are all substantially parallel to the longitudinal axis. The beveled corners 80 are oppositely located and the cross-section has a generally square or rectangular geometric shape. With respect to the main body 64, the top surface 70 and the bottom surface 68 of the main body 64 are interconnected by two ends 82 and two sides 84. The two ends 82 are opposite from each other and have a generally convex surface. The two sides 84 are opposite from each other and have a generally concave surface. Together, the two ends 82 and the two sides 84 define an elongate, rectangular-like shape when viewed from the top with the two sides 84 having a length that is greater than the length of the two ends 82. Although a rectangular or elongate shape is shown in the figures, the main body 48 can have any other suitable shape such as elliptical or circular.

Figure 21:
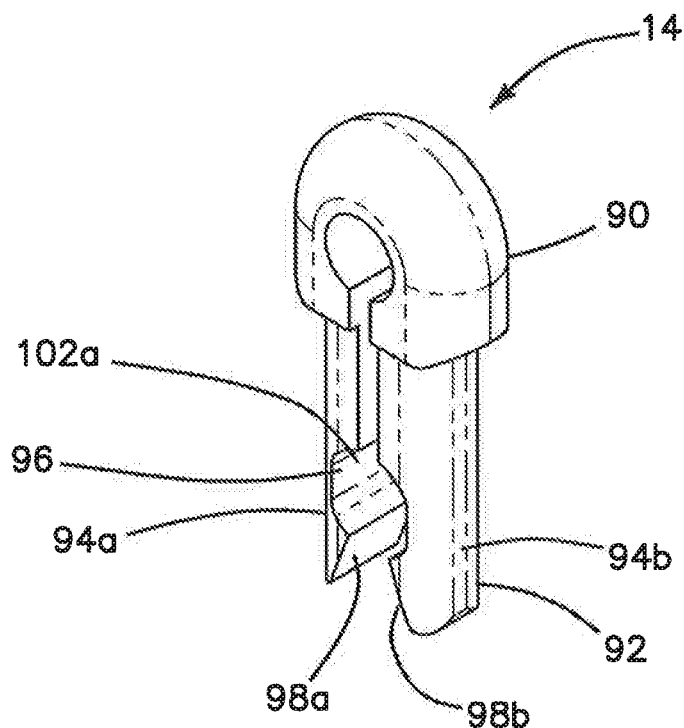
FIG. 21 is a top perspective view of a retainer according to the present invention.
Figure 22:
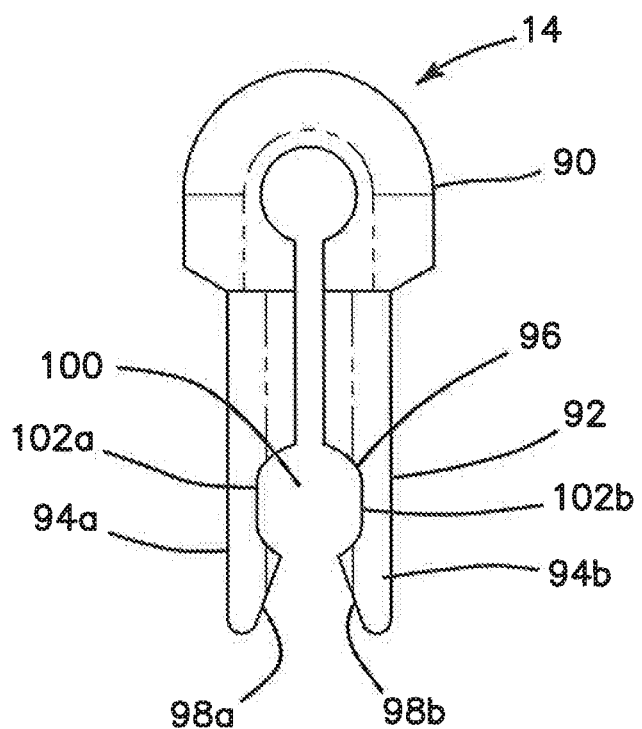
FIG. 22 is a side front elevational view of a retainer according to the present invention n.
Figure 23:
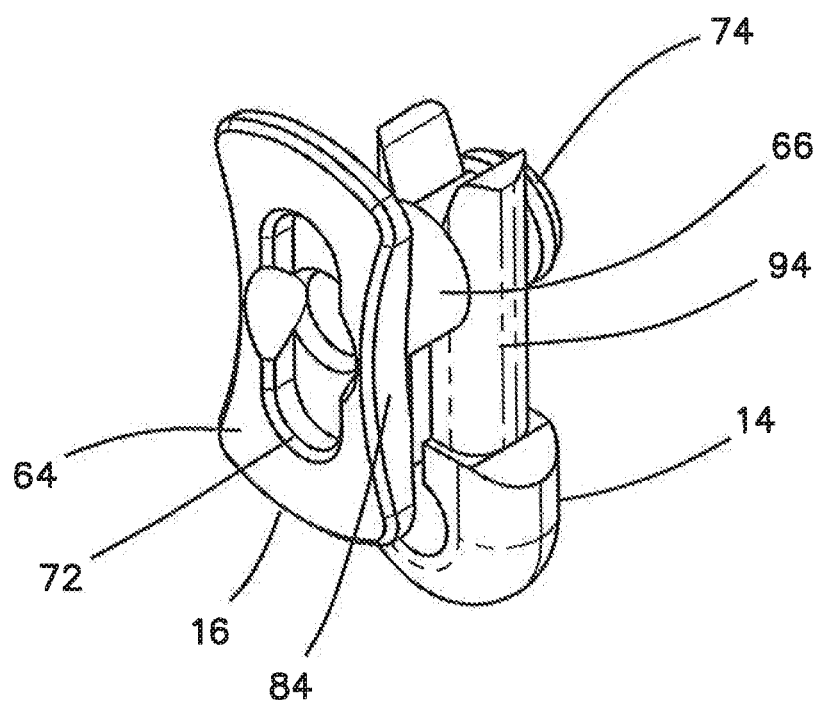
FIG. 23 is a top perspective view of a retainer and lock in an unlocked configuration according to the present invention.
Figure 24:
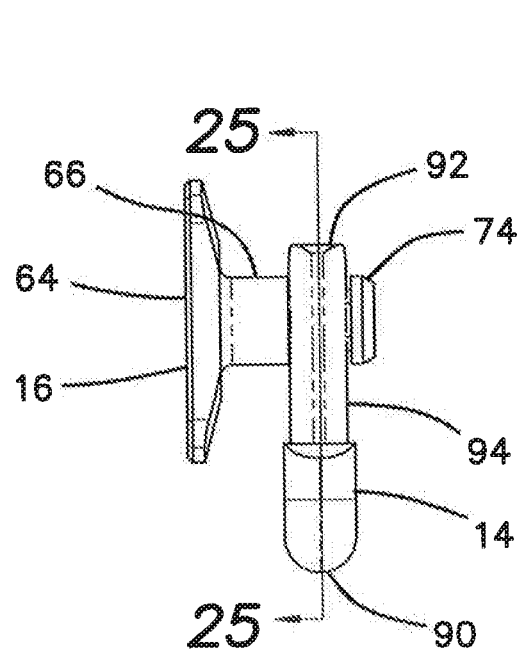
FIG. 24 is a side view of a retainer and lock in an unlocked configuration according to the present invention.
Figure 25:
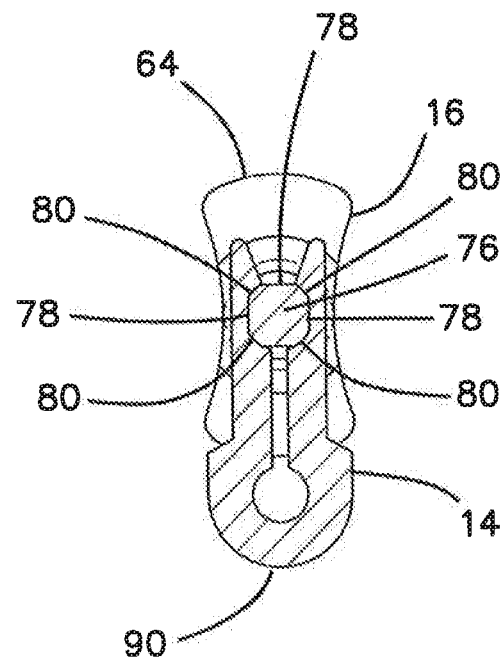
FIG. 25 is a cross-sectional view taken along line 25-25 of FIG. 24 of a retainer and lock in an unlocked configuration according to the present invention.
Figure 26:
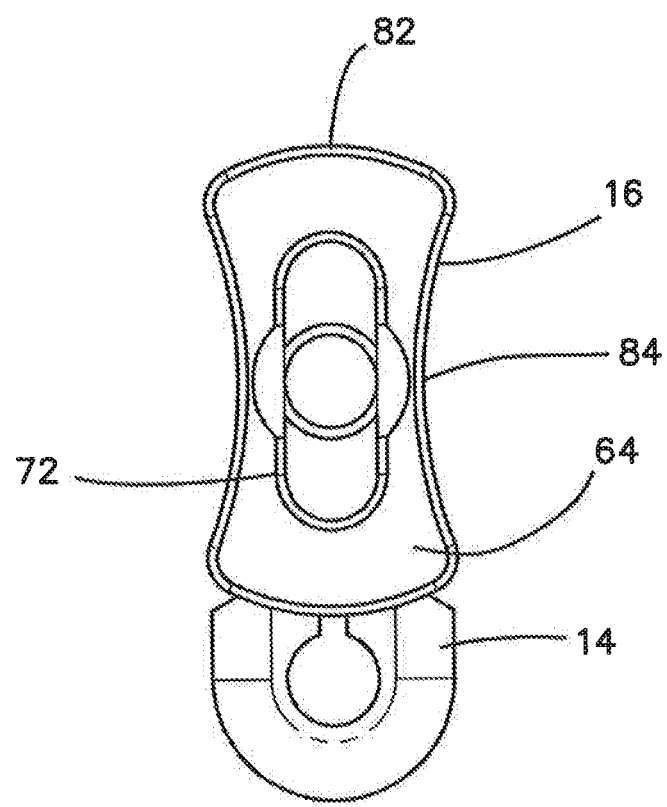
FIG. 26 is a front elevational view of a retainer and lock in an unlocked configuration according to the present invention.
Figure 27:
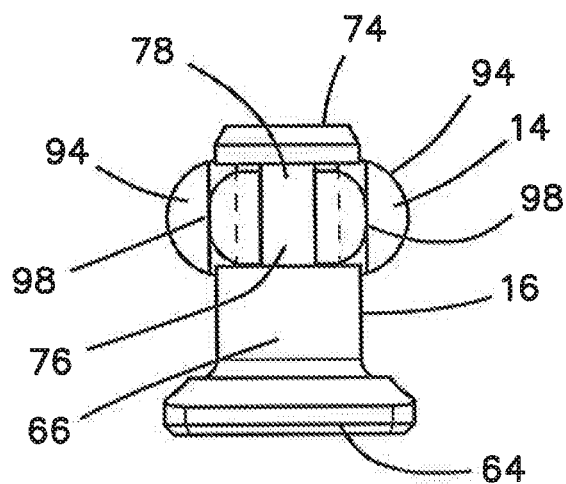
FIG. 27 is a top planar view of a retainer and lock in an unlocked configuration according to the present invention.

Turning now to FIGS. 21-22, the lock retainer 14 will now be described in greater detail. The lock retainer 14 has a proximal end 90 and a distal 92. The distal end 92 includes two prongs 94a, 94b defining a gap therebetween. Each prong 94a, 94b has an angled tip 98a, 98b to define a ramped entry in the proximal direction. The lock retainer 14 includes a lock receiving location 96 near the distal end 92 that is sized and configured to receive at least a portion of the lock 16 to hold the lock 16 connected to the cage 12. In one variation, the lock receiving location 96 is defined by and formed in the pronged distal end 92. In particular, the lock receiving location 96 includes an opening 100 formed in part by each prong 94a, 94b and the gap between the prongs. The inner surface of each prong 94a, 94b includes at least one lock-engaging surface 102a, 102b. The lock-engaging surfaces 102a, 102b together complement the shape of the neck 76 of the lock 16. In particular, the lock-engaging surfaces 102a, 102b complement at least two facets of the neck 76. In the variation shown in the figures, the lock-engaging surfaces 102a, 102b complement two sides 78 of the neck 76. The prongs 94a, 94b are capable of flexing outwardly in a cantilever spring-like manner to increase the size of the gap therebetween and inwardly to return to a normal unstressed position.

Figure 2:
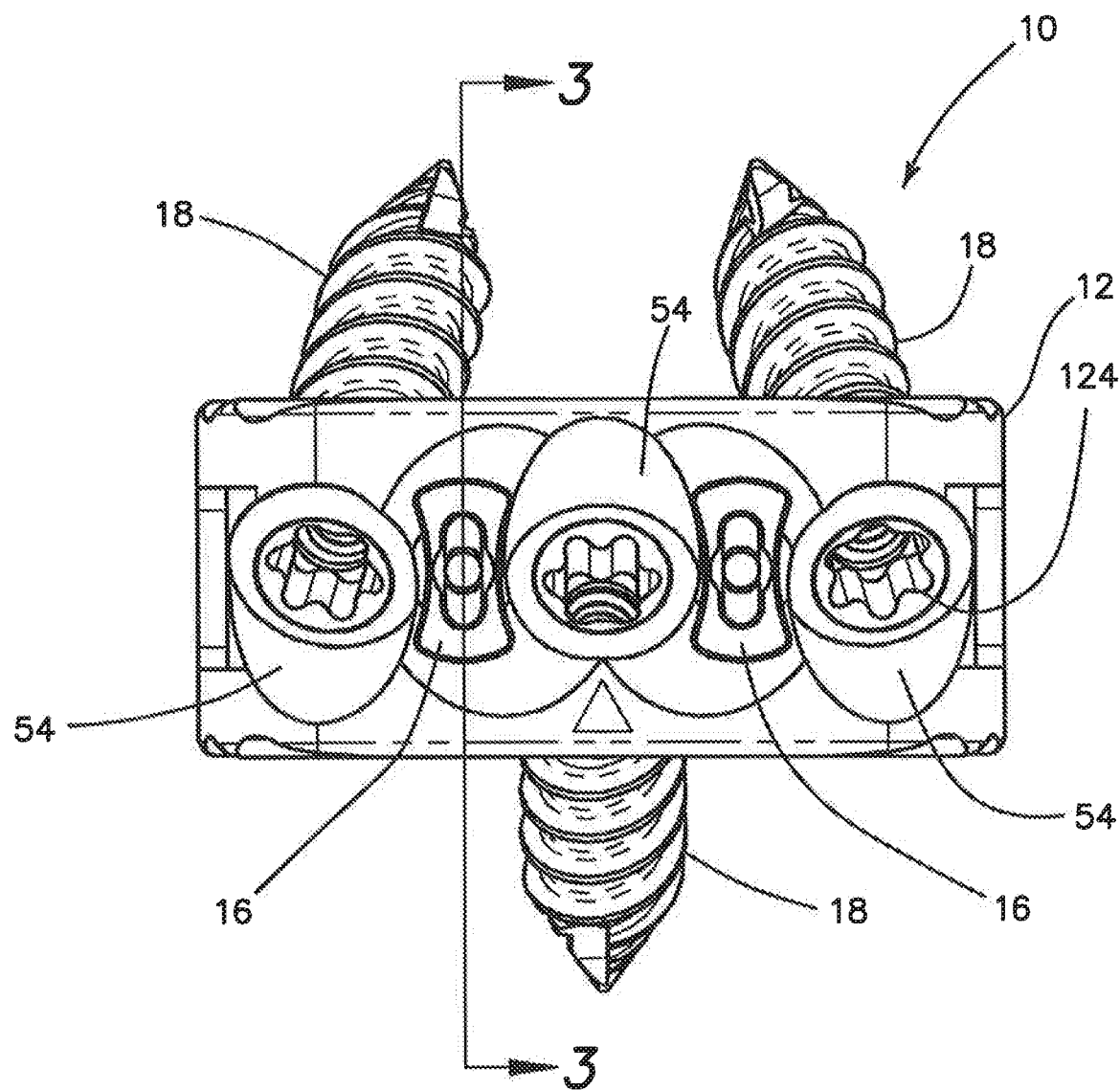
FIG. 2 is a front elevational view of an interbody spacer in an unlocked configuration according to the present invention.
Figure 3:
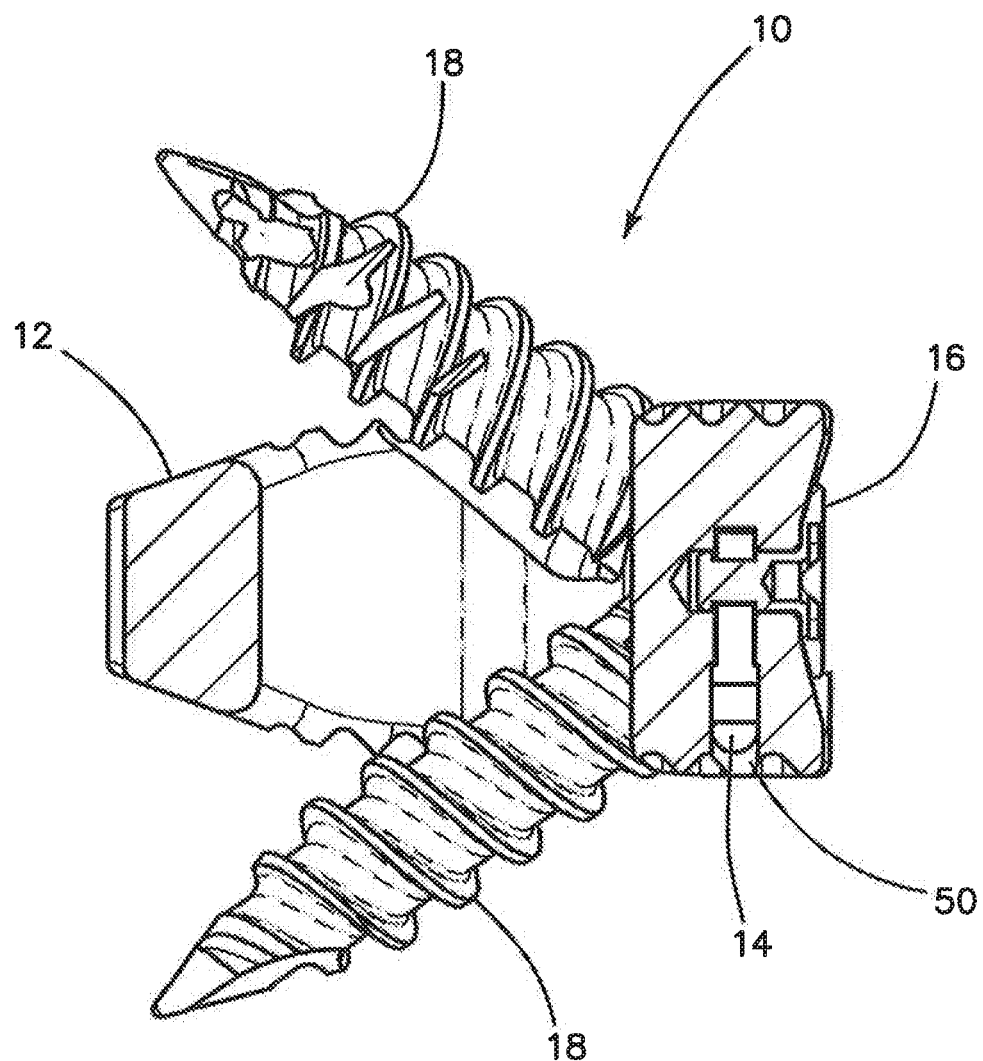
FIG. 3 is a cross-sectional view taken along line 3-3 of FIG. 2 of an interbody spacer in an unlocked configuration according to the present invention.
Figure 4:
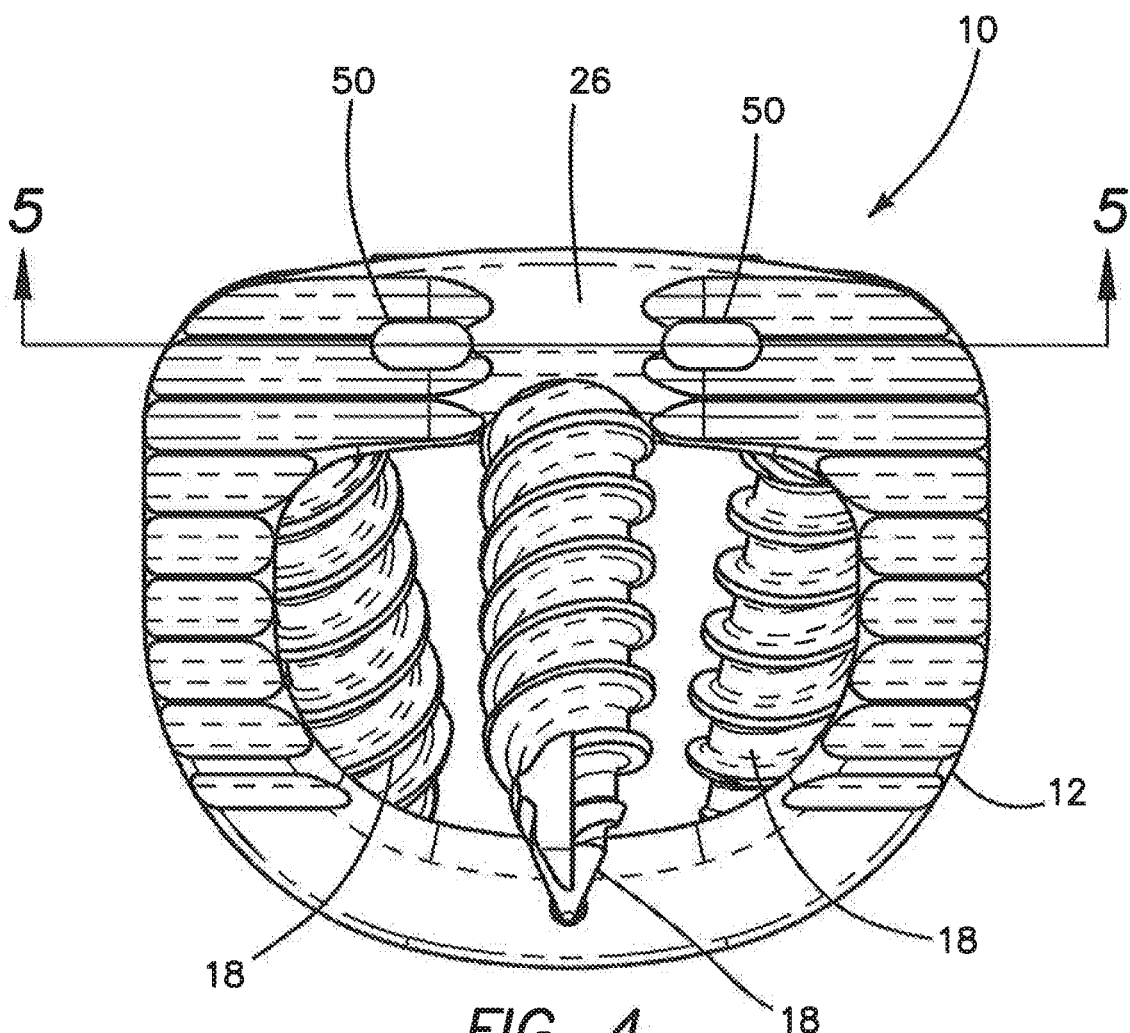
FIG. 4 is a bottom planar view of an interbody spacer in an unlocked configuration according to the present invention.
Figure 5:
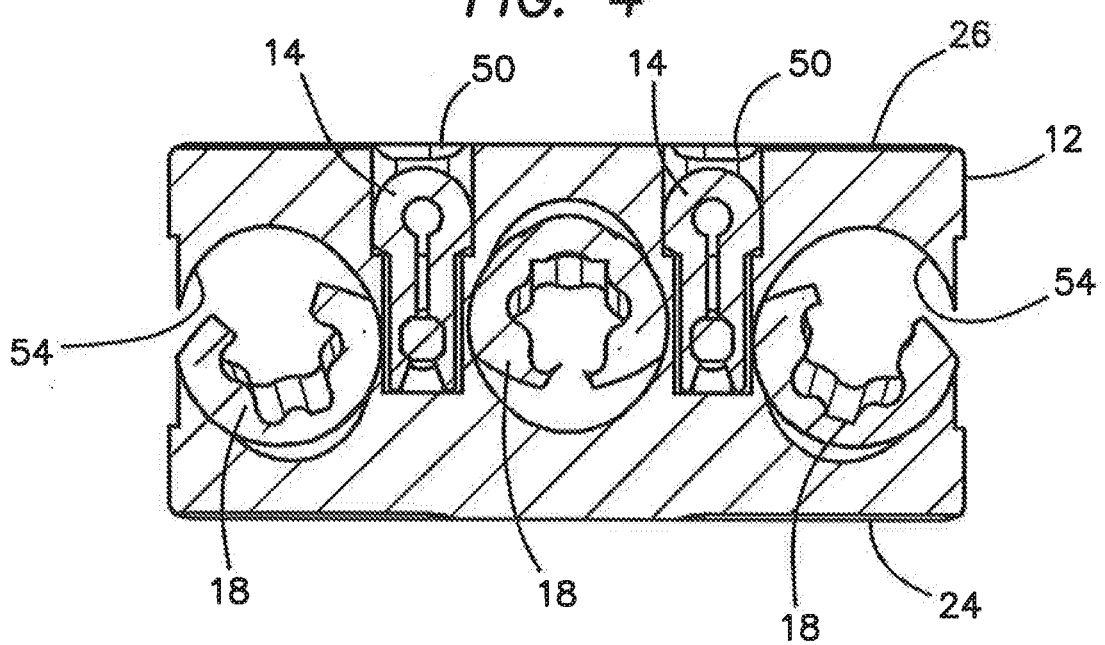
FIG. 5 is a cross-sectional view taken along line 5-5 of FIG. 4 of an interbody spacer in an unlocked configuration according to the present invention.
Figure 6:
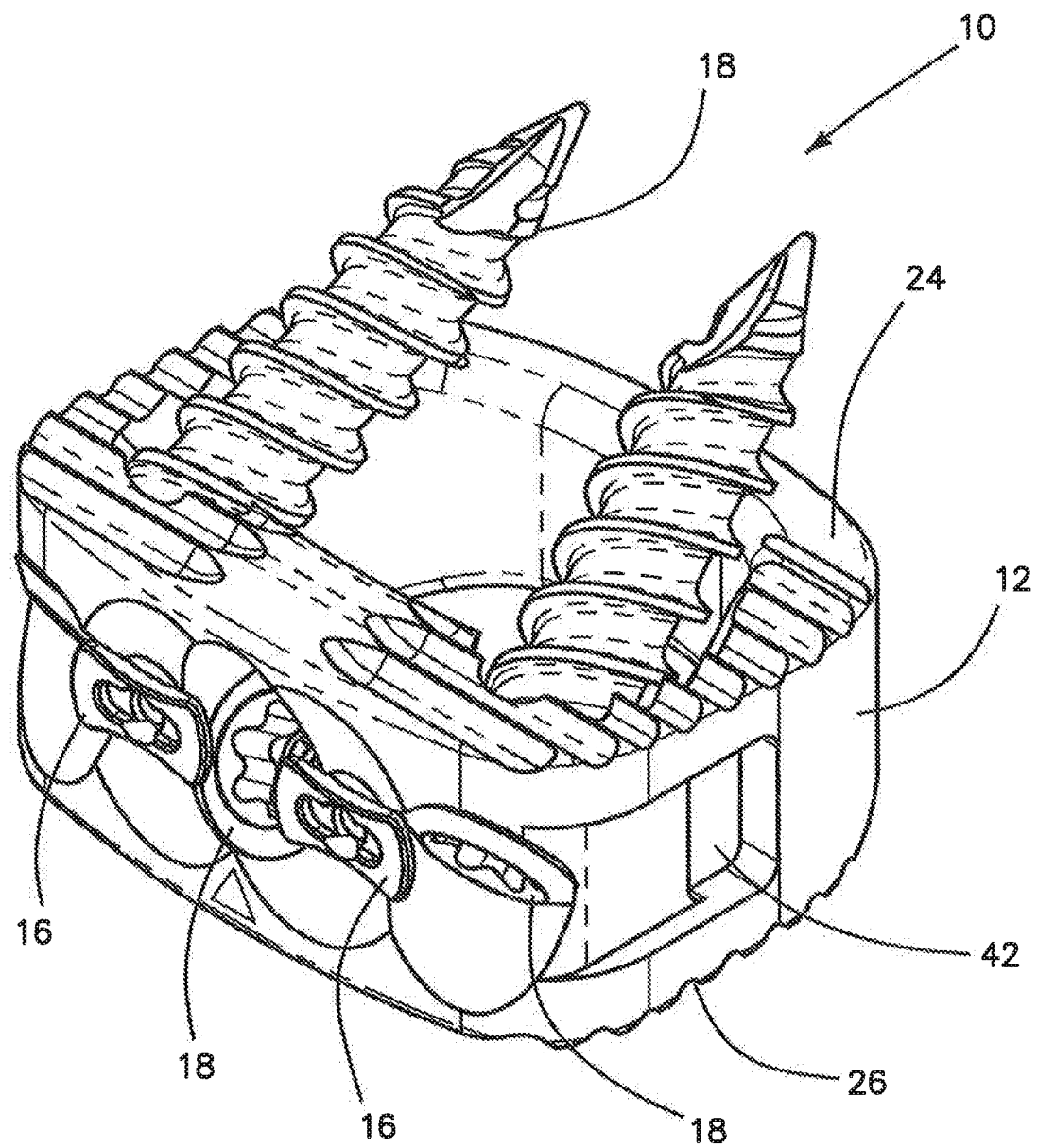
FIG. 6 is a top perspective view of an interbody spacer in a locked configuration according to the present invention.
Figure 7:
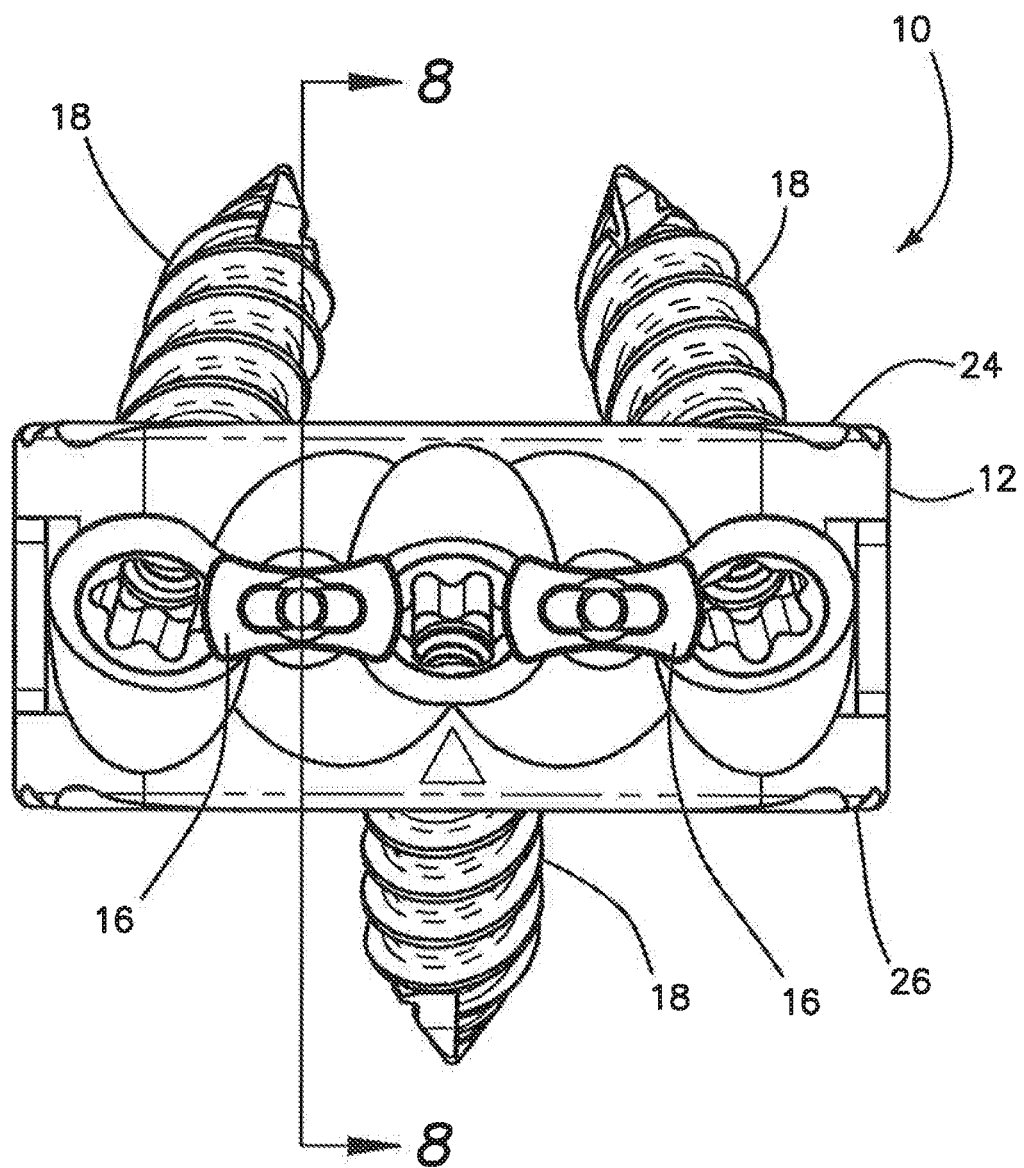
FIG. 7 is a front elevational view of an interbody spacer in a locked configuration according to the present invention.
Figure 8:
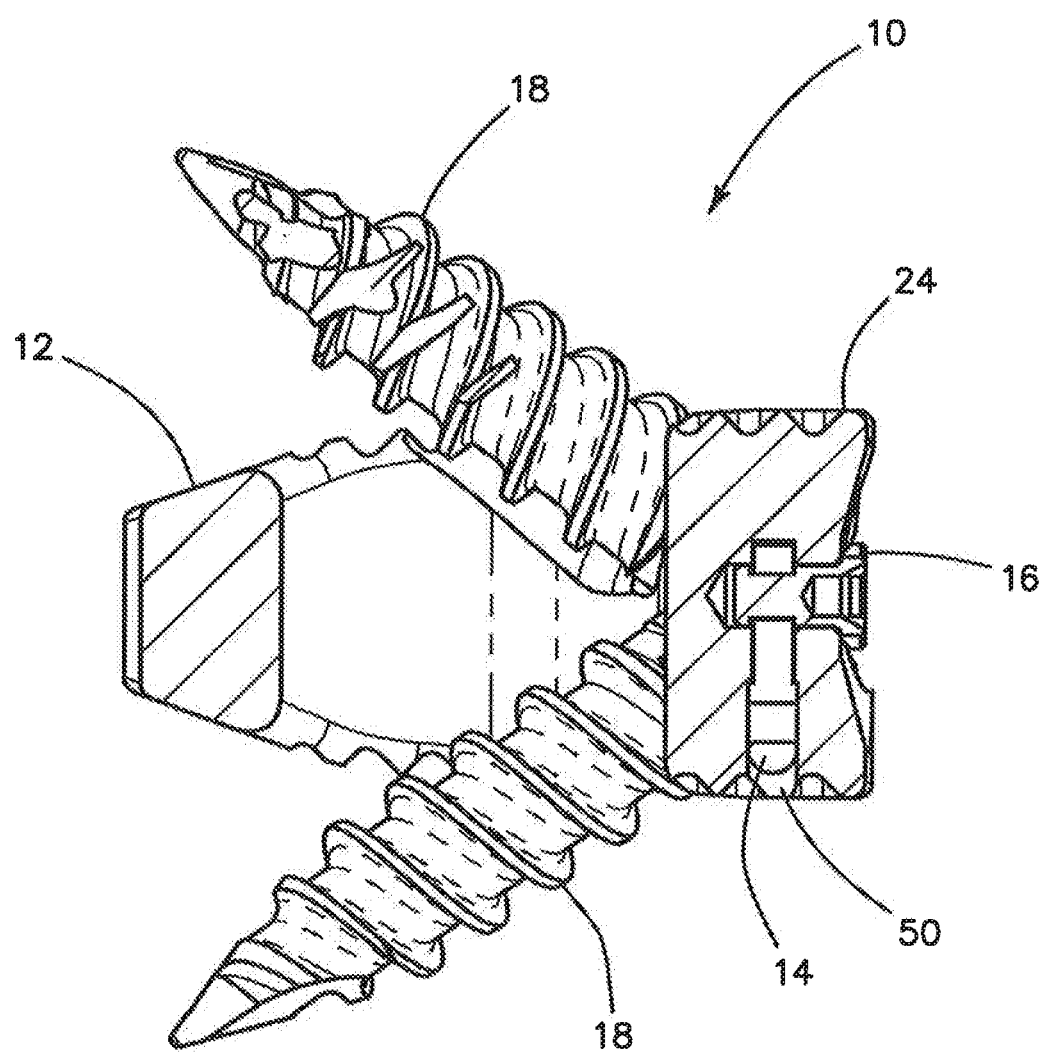
FIG. 8 is a cross-sectional view taken along line 8-8 of FIG. 7 of an interbody spacer in a locked configuration according to the present invention.
Figure 9:
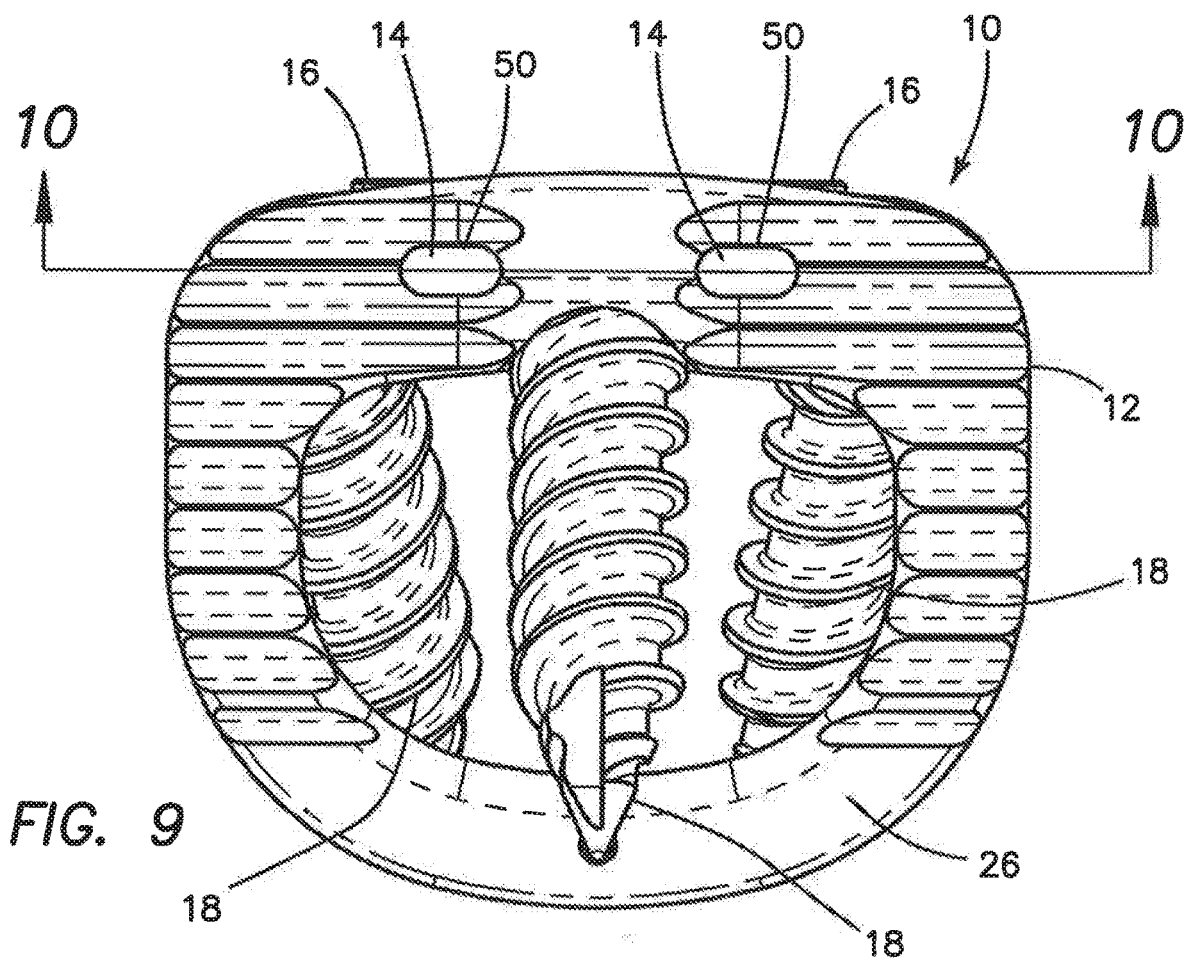
FIG. 9 is bottom planar view of an interbody spacer in a locked configuration according to the present invention.
Figure 10:
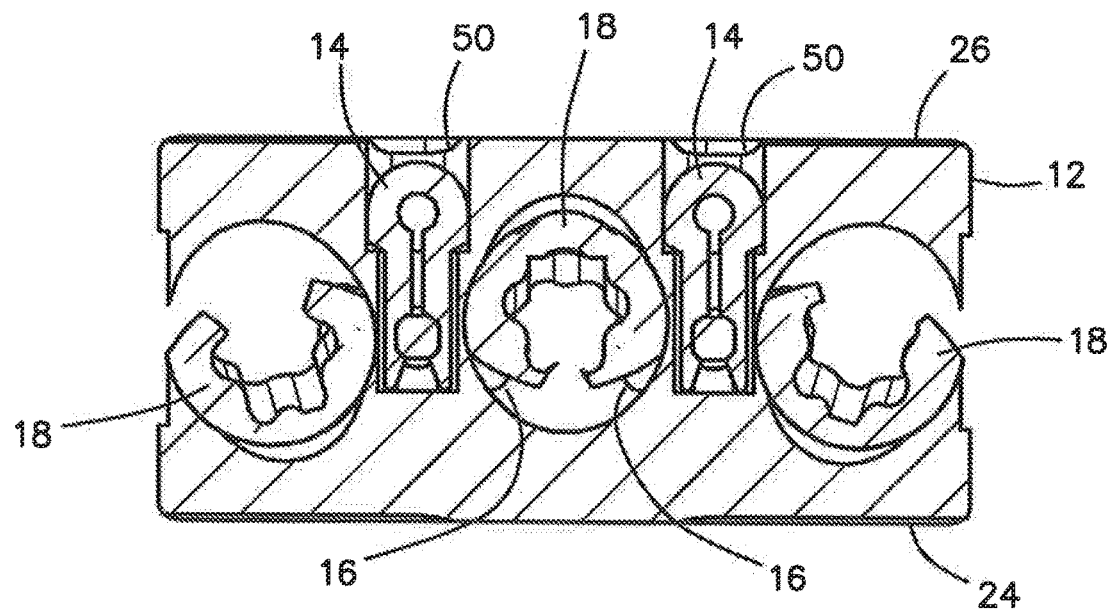
FIG. 10 is a cross-sectional view taken along line 10-10 of FIG. 9 of an interbody spacer in a locked configuration according to the present invention.
Figure 11:
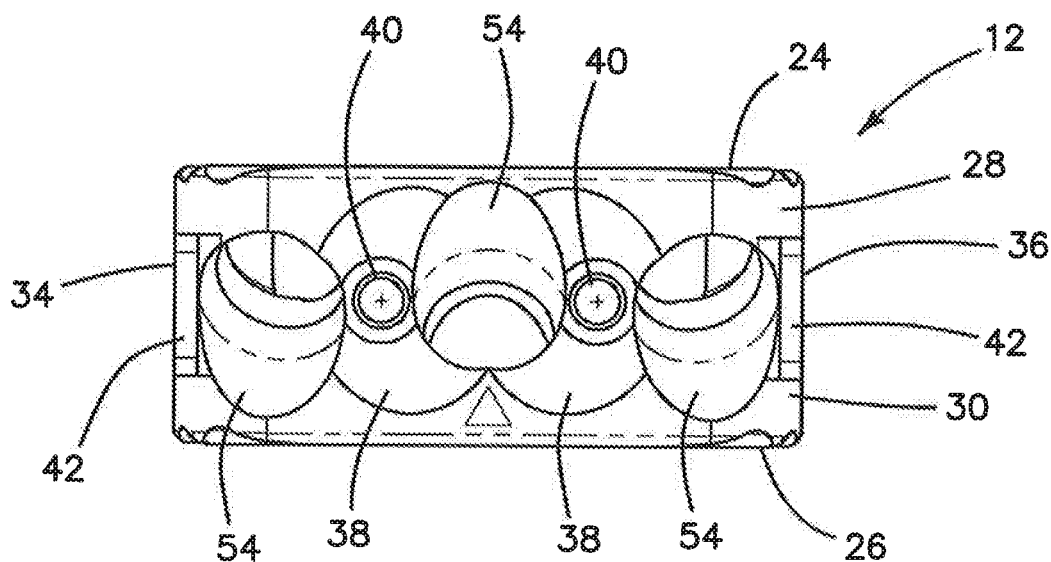
FIG. 11 is a front elevational view of a cage according to the present invention.
Figure 12:
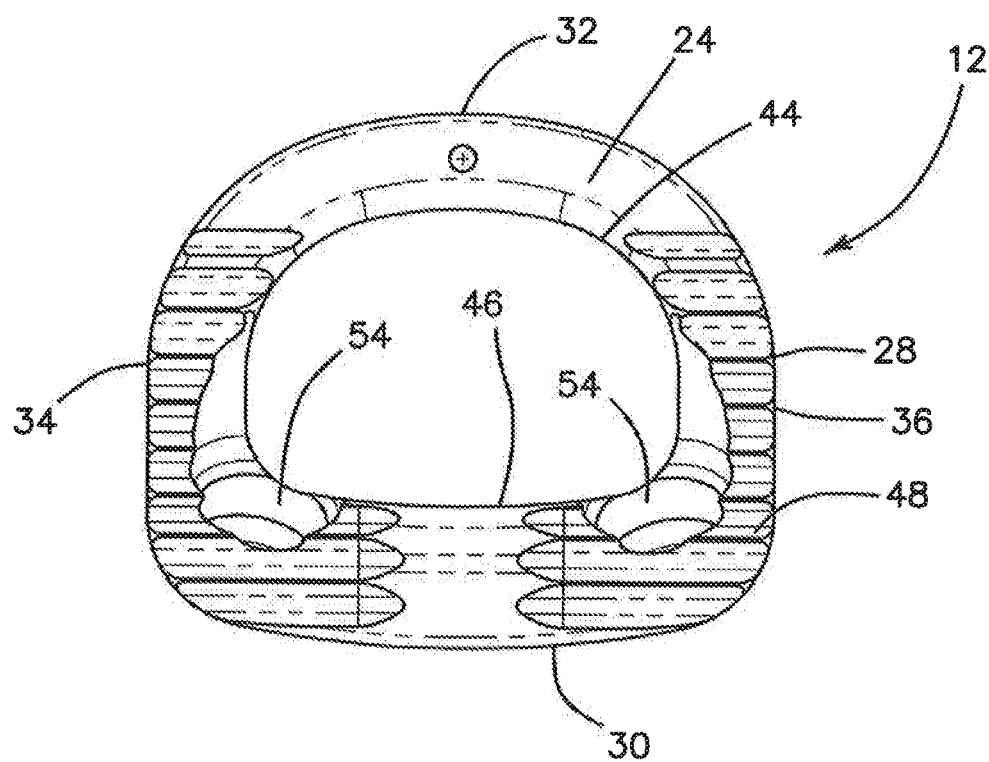
FIG. 12 is a top planar view of a cage according to the present invention.
Figure 13:
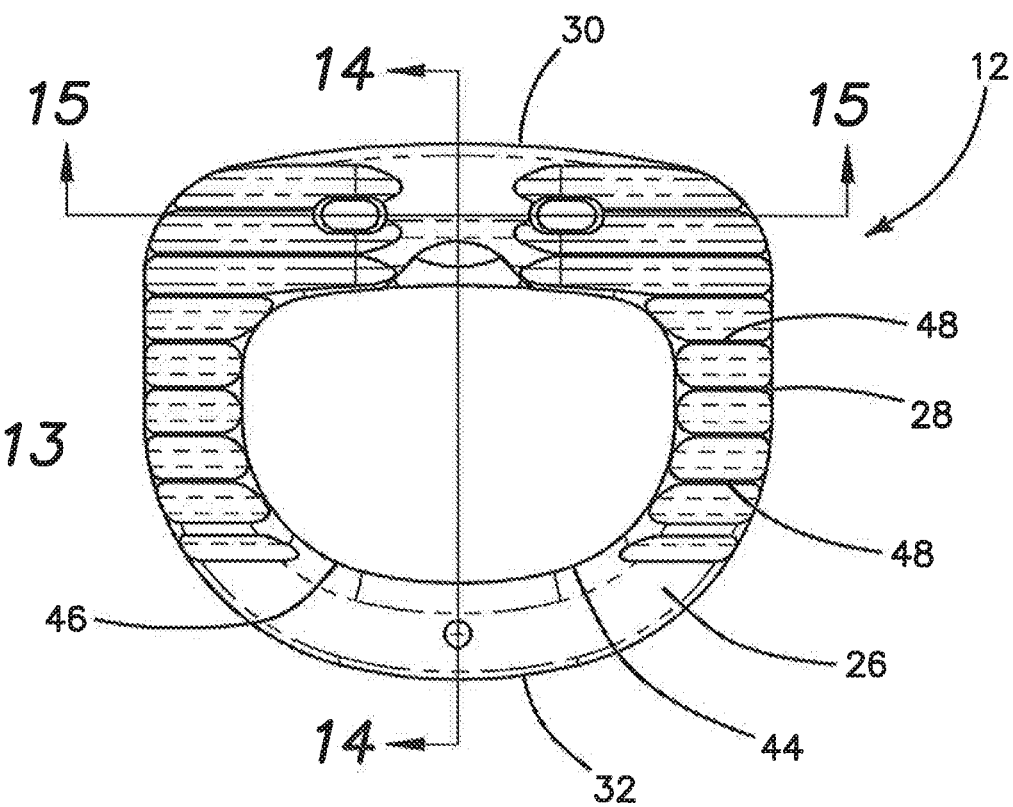
FIG. 13 is a bottom planar view of a cage according to the present invention.
Figure 15:
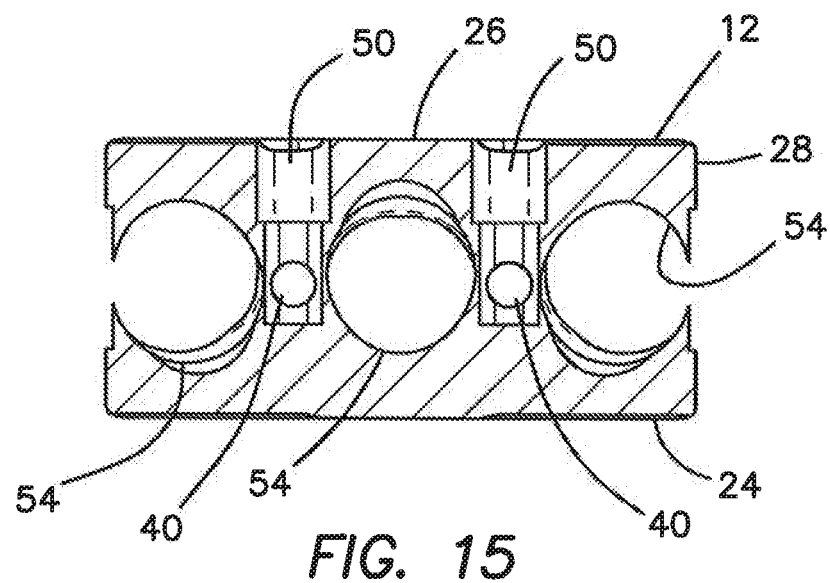
FIG. 15 is a cross-sectional view taken along line 15-15 of FIG. 13 of a cage according to the present invention

With reference back to FIGS. 1 and 2, the bone screw 18 will now be described in greater detail. The bone screws 18 used with the cage are exemplary orthopedic fasteners that are preferably used with the interbody spacer 10 of the present invention although other types of fasteners may be employed. The bone screw 18 includes a screw head 118, neck and threaded shank 122. The head 118 is bulbous having a larger lateral dimension than the threaded shank 122. Also, the outer surface of the head 118 is curved, spherical in shape or partially spherical or a frustum or frusta of a sphere having a region of a sphere delimited by one plane parallel to a plane containing a diameter or having a region of a sphere delimited by two planes which in one variation may be parallel to each other. The proximal plane of the frusta-spherical head 118 includes an opening that serves as an instrument recess or socket 124 configured to engage a complementary tip of a surgical tool for driving the bone screw into bone. A substantially hexagonal, daisy-shaped recess 124 is shown in FIG. 2; however, the recess 124 can be of any shape that allows a surgical tool to drive the bone screws 18 into the vertebral column. The head 118 of the bone screw 18 corresponds to the shape of the bone screw apertures 54 in the cage 12. The bone screws 18 are configured to allow polyaxial, variable angle or fixed angled orientation with respect to the cage 12 while disposed inside the bone screw apertures 54. The angulation of the bone screws 18 with respect to the cage 12 allows a desired angle or orientation with respect to the cage 12 and adjacent vertebral bodies to be achieved to anchor the cage 12 to the vertebrae. The bone screws 18 are preferably self-tapping and configured for insertion into bony material, however, other screws requiring holes to be drilled or pre-tapped can also be employed.

The cage 12 is typically made of a polymer such as polyether ether ketone (PEEK) which is a thermoplastic polymer that has been widely accepted for use in the manufacture of medical implants. PEEK has excellent mechanical, chemical resistance and biocompatible properties and has been finding increased use in spinal fusion devices as it mimics the stiffness of real bone. While many medical implants are made entirely of PEEK, many implants have both PEEK components and non-PEEK components such as stainless steel and titanium. The cage 12 may also be made of metal. The bone screws 18, lock 16 and lock retainer 14 are made of metal such as surgical stainless steel and titanium.

The interbody spacer 10 is assembled by inserting a lock 16 into each of the lock apertures 40. With the locks 16 in position, a lock retainer 14 is inserted into the retainer openings 50. The lock aperture 40 intersects with the retainer opening 50 such that the neck 76 of the lock 16 is engaged by the prongs 94 of the retainer 14. In particular, the angled tips 98 will contact the neck 76 such that the neck 76 is substantially situated in the gap between the two prongs 94a, 94b. With the continued force of insertion, the flexible prongs 94a, 94b splay apart and ramp around the neck 76 until the neck 76 is positioned within the lock-receiving location 96 between the prongs 94a, 94b. With the neck 76 located in the lock-receiving location 96, the prongs 94 will spring back toward their relaxed state with two opposite sides 78 of the neck 76 being in juxtaposition with the opposite lock-engaging surfaces 102. With the neck 76 surrounded in part by the retainer 14, lateral displacement of the lock with respect to the cage 12 is prevented. Furthermore, displacement of the lock in the proximal direction is prevented by the distal stop 74. For example, if moved in the proximal direction, the distal stop 74 of the lock 16 will abut the prongs 94 and prevent removal of the lock 16. The lock retainer 14 is also prevented from falling out of the cage 12 after snapping around the neck 76 of the lock 16 and being hooked around the neck 76. The lock 16 and lock retainer 14 are connected to the cage 12. In one variation, the retainer opening 50 is sized and configured to connect the retainer 14 to the cage 12 in a friction-fit, snap-fit or other engagement. In another variation, the lock aperture and the retainer opening 50 are intersect in a coaxial manner and share the same longitudinal axis. The ramped surface of each of the angled tips 98 eases the insertion of the lock retainer 14 and the wide, inner proximal end of the angled tip 98 serves as an abutment preventing removal of the lock retainer 14. The lock 16 is connected to the cage 12 via the lock retainer 14 in such a manner that the lock is permitted to rotate with respect to the cage 12 between an unlocked configuration and a locked configuration. Bone screws 18 are inserted into the bone screw apertures 54 when the locks 16 are in an unlocked position before surgery or in-situ during surgery.

With reference to FIGS. 23-27, the lock 16 and the retainer 14 are shown in an unlocked configuration. The unlocked configuration is also shown in FIGS. 1-5. When in the unlocked configuration, the locks 16 are oriented substantially vertically, parallel to the longitudinal axis of the cage 12. The curved sides 84 of the main body 64 of the lock 16 face the bone screw apertures 54. The curvature of the sides 84 provides clearance for the pathway for the insertion of bone screws 18 and advantageously allows the interbody spacer 10 to be made smaller in the lateral dimension. In an unlocked configuration, with the bone screws 18 inserted, one or more side 84 is in juxtaposition with the one or more inserted the bone screws 18. The unlocked configuration permits unhampered insertion and removal of bone screws 18. When inserted, the shape of the bone screw apertures 54 permit the bone screws 18 to angulate polyaxially with respect to the cage 12 for ideal positioning into bone.

With reference to FIGS. 28-32, the lock 16 and the retainer are shown in a locked configuration. The locked configuration is also shown in FIGS. 6-10. When in the locked configuration, the locks 16 are oriented substantially horizontally or perpendicular to the longitudinal axis of the cage 12; however, the invention is not so limited and the locks 16 need only be angled away from the vertical orientation parallel to the longitudinal axis to effect a locked configuration in which at least a portion of the main body 64 covers one or more bone screw heads 118 to prevent them from backing out with respect to the cage 12. The distance between the ends 82 of the main body 64 is longer than the distance between the sides 84 of the main body 64. The long length of the main body is moved away from its vertical orientation to cover the bone screw 18. When the lock 16 is rotated from an unlocked configuration toward a locked configuration, the main body 64 of the lock 16 because of its shape will move into the space of the bone screw apertures 54 where the bone screws 18 reside. Rotation of the lock main body 64 continues until at least a portion of the main body 64 covers the head 118 of the bone screw 18 to prevent backing out of the screw 18. The degree of rotation required to prevent the backing out of screws will vary depending upon the angulation of the bone screw 18, the final positioning of the bone screw 18 with respect to the anatomy and the arrangement of the lock 16 with respect to the cage 12. As shown in the figures, the lock 16 is free to rotate 360 degrees about its axis. In other variations, the lock 16 may be restricted to movement of approximately 90 degrees. In the variation shown in the figures, a rotation of the lock 16 between approximately 0 and 180 degrees will effect a locked configuration preventing the back out of screws. Advantageously, this wide range permits even a small rotation such as 20 degrees to cover the bone screw 18 and this small rotation can be made in either a clockwise or counterclockwise direction to simultaneously cover two adjacent bone screws 18 with one lock 16. The system also advantageously permits the surgeon to achieve an ideal positioning of the bone screws 18 without having to worry about achieving a successful locking orientation and having to reposition a bone screw to ensure a locked configuration. In other words, if due to the patient anatomy, the bone screw 18 placement is highly askew, the rotating lock of the present invention can be rotated in a clockwise or counterclockwise direction and between 0 and 180 degrees to cover a bone screw 18 to achieve back out protection; whereas, in other designs of cages that require a plate to cover the screw heads, the cover plate may not be able to be positioned due to the askew bone screw and as a result requiring a tradeoff between bone screw positioning/re-positioning and back-out protection. The present invention advantageously offers wide flexibility for bone screw placement while at the same time offering a wide coverage for a locked configuration of one or more bone screws. In another variation, the main body of the lock is not symmetrical in a cross-section taken perpendicular to the longitudinal axis and may be, for example, lobed in one direction.

As mentioned above, the lock 16 is rotatable with respect to the cage 12. In one variation, a freely rotating lock 16 is provided in which the neck 76 is not faceted. In the variation shown in the figures, the lock 16 is free to rotate; however, metered, incremental rotation of the lock 16 with respect to the lock retainer 14 is provided due to the faceted shape of the neck 76. The faceted neck 76 advantageously prevents inadvertent movement of the main body 64 of the lock 16 into the insertion pathway of the bone screw and, thereby, prevents interference with bone screw placement. To rotate the lock 16, an instrument having a distal end that is complementary to the size and shape of the socket 72 formed in the top surface 70 of the main body 64 is used. As the lock 16 is rotated from the unlocked position in either a clockwise or counterclockwise direction, the diagonal distance of the cross-section of the neck 76 taken perpendicular to the longitudinal axis will come into contact and engage the lock-engaging surface 102 of the retainer 14. Since the diagonal distance or length, as measured from the center of one beveled corner 80 to the center of another beveled corner 80 that is located diagonally across is longer than the side 78 to side 78 distance width of the neck, rotation will splay the prongs 94 slightly apart in a cam-like action before snapping into a completed approximately 90 degree rotation of the lock 16 around its longitudinal axis in which two opposite sides 78 will come into contact with the lock-engaging surfaces 102 on the prongs 94. Thereby, the cross-sectional shape of the neck 76 against the lock-engaging surfaces 102 inside the opening 100 of the lock 16 provides an incremental rotation of 90 degrees. The post can have any irregular shape such that its rotational motion gives the prongs/retainer that is in contact with the post a specific rocking or reciprocating cam-like motion. The cross-section of the neck 76 may have a different number of facets than the four sides shown in the figures. For example, a neck 76 can have three sides to form a triangular-shaped cross-section or an octagonal shaped cross-section as seen fit to increase the number of increments in the rotation around the perimeter and reduce the arc of rotation as needed. The incremental rotation advantageously provides tactile feedback to the surgeon of successfully establishing a locked configuration as well as to the number of rotations of the lock.

In addition to the advantages of the interbody spacer 10 of the present invention noted above, the interbody spacer 10 according to the present invention provides a preassembled cage and lock assembly. This assembly advantageously allows the surgeon to simply position the implant between vertebrae drive the bone screws into the bone and rotate the lock into a locked configuration. The surgeon is not required to pick-and-place a cover plate onto the anterior side of the cage to cover the bone screws. The surgeon is also not required to pick-and-place a plate screw and drive the plate screw to secure the cover plate to the cage either in-situ or in assembly.

In use, the present interbody spacer 10 is configured for use as an ALIF cage in spinal surgical procedures. It is understood that novel features of the present invention can find application in different types of cages including but not limited to interbody spacers for PLIF, TLIF, XLIF surgical procedures as well as other types of orthopedic implants. Implanting the interbody spacer 10 involves removal, in whole or in part, of the disc material from the intervertebral space at the target vertebral level where the interbody spacer 10 will be implanted. The patient is oriented to provide some distraction of the disc space and to provide access to the anterior of the spine. Additional distraction of the disc space and surrounding tissues may be needed to decompress the nerve roots, realign the anatomical axis of the spine, and restore disc space height at the particular target level. After disc material is removed, a clean space is achieved in which to place the device. The vertebral endplates may be further prepared using burrs, curettes and the like to abrade and clean the endplates to encourage bone regeneration. A surgeon will then select an appropriately sized cage 12 that has the best size in footprint and height and lordotic angle for the target space. The surgeon may use an insertion instrument to grasp the cage 12 and place it at the mouth of the intervertebral space and move and orientate the cage 12 into its proper orientation within the intervertebral space. The insertion instrument typically has two distal prongs configured to securely attach to the cage 12 at the instrument notches 42. The surgeon may determine the position of the cage 12 with the help of one or more x-ray fluoroshots. Since the position of the radiographic markers are known relative to the cage 12, a surgeon can determine the position of the cage 12 in the target space by viewing the positions of the radiographic markers embedded in the cage 12 that appear in the x-ray and reposition the cage 12 as needed until final placement is achieved. The cage 12 may include bone graft or other material located inside the central opening 44 of the cage 12 to promote ingrowth and blood supply in order to grow active and live bone from the adjacent spinal vertebrae to inter-knit with the spacer 10 and, thereby, eventually immobilize and fuse the adjunct spinal vertebrae. The cage 12 is placed such that the anterior surface 30 of the cage 12 faces the anterior side of the patient and the top surface 24 contacts the lower endplate of the upper vertebral body and the bottom surface 26 of the cage 12 contacts the upper endplate of the lower vertebral body on either side of the target intervertebral space. The geometry of the ridges 48 on the top surface 24 and the bottom surface 26 provide resistance to migration of the cage 12 while inside the target space. Other coatings and surface textures may also be provided on the cage 12. Next, bone screws 18 are deployed via a surgical instrument such as a bone screw driver. The bone screws 18 are inserted into the bone screw apertures 54 and tapped into the bone of the adjoining vertebral bodies. The one or more bone screws 18 are passed through the cage 12 via the bone screw apertures 54 in a trajectory transverse to the longitudinal axis and into the upper and lower vertebral bones. As the bone screws 18 are tightened, the vertebral bodies penetrated with the bone screws 18 will compress onto both sides of the load-bearing cage 12 and provide pressure to help facilitate fusion. Additional bone graft material may be placed in the intervertebral disc space. Next, the locks 16 are rotated clockwise or counterclockwise as needed with an instrument inserted to the socket 72 of the lock 16 to bring the lock 16 from an unlocked configuration to a locked configuration to provide an anti-backout mechanism to prevent the bone screws 18 from loosening and/or exiting the cage 12. With the lock 16 in a locked configuration, the lock 16 is disposed over a head 118 of at least one of the adjacent bone screws 18 implanted together with the cage 12. The lock provides anti-back-out protection for the bone screws 12. In one variation, because the bone screws 18 are partially covered, the bone screws are permitted to angulate at a greater angle. The bone screws 18 are shown at a given angle although any suitable angle(s) for a given application may be utilized and as may any suitable number of screws. Additional instrumentation such as rods or screws may also be used to further stabilize the spine across the target level. Any of the components in the present invention are manufactured from metal such as titanium, ceramic, plastic such as PEEK and carbon fiber reinforced polymer, biomaterial including but not limited to any of a number of biocompatible implantable polymers including PEKK, PEKEK, polyetheretherketone (PEEK) being preferred, titanium ceramic, bone or other material etc. The present invention can be employed and is suitable for use where ever the backing out of screws is to be prevented and anywhere along the spine including but not limited to cervical, thoracic, lumbar or sacral or between other bony structures outside of the spinal region. Embodiments of the present invention are standalone interbody devices which may be designed in the general style of an ALIF device, TLIF device, PLIF device or other device. In addition, the size and/or shape of the basic embodiments disclosed herein may be adapted by one skilled in the art for use in various levels of the spine, namely the cervical spine, thoracic spine and the lumbar spine. Thus, while various embodiments herein may be described by way of example with respect to the lumbar spine such disclosures apply with equal weight to the other levels of the spine.

It is understood that various modifications may be made to the embodiments of the interbody spacer disclosed herein. Therefore, the above description should not be construed as limiting, but merely as exemplifications of preferred embodiments. Those skilled in the art will envision other modifications within the scope and spirit of the present disclosure.

We claim:

1. An interbody spacer system for a spine, comprising:
a cage having a top surface and a bottom surface interconnected by a sidewall; the cage includes a central opening extending between the top surface and the bottom surface and defining an inner surface; the cage includes at least one bone screw aperture in the sidewall; the cage includes a lock aperture; the cage includes a retainer opening that intersects with the lock aperture;
at least one bone screw disposed inside the at least one bone screw aperture; each bone screw having a head at a proximal end and a threaded shank extending toward a distal end for anchoring into bone; the bone screw being configured to secure the interbody spacer between two bony components of the spine; and
a lock connected to the cage and located inside the lock aperture; the lock having an unlocked position in which the lock does not cover the head of the bone screw inside the bone screw aperture permitting passage of the bone screw in or out of the bone screw aperture and a locked position in which at least part of the lock is above the head of the bone screw to prevent the bone screw from backing out of the bone screw aperture; wherein rotation of the lock moves the lock between the unlocked position and the locked position; and wherein the lock includes a main body connected to a post; the post extending along a longitudinal axis of the lock; the post having at least two oppositely disposed, flat surfaces parallel to the longitudinal axis of the lock; and
a retainer located in the retainer opening and coupled to the lock such that the lock is retained and permitted to rotate with respect to the cage; the retainer defines a lock-receiving location; wherein the lock-receiving location is sized and configured to receive at least a portion of the lock; and the lock-receiving location having two oppositely disposed, flat lock-engaging surfaces parallel to the longitudinal axis.

2. The interbody spacer system of claim 1 wherein the post is located inside the lock aperture and the main body covers the head of the bone screw in the locked position.

3. The interbody spacer system of claim 1 wherein the retainer opening defines a longitudinal axis and the lock aperture defines a longitudinal axis; wherein the longitudinal axis of the retainer opening is perpendicular to the longitudinal axis of the lock aperture.

4. The interbody spacer system of claim 1 wherein the retainer includes two prongs at a distal end of the retainer; and the lock-receiving location being located between the two prongs.

5. The interbody spacer system of claim 4 wherein each prong includes an angled tip.

6. The interbody spacer system of claim 4 wherein the two prongs flex outwardly away from each other and spring back to capture at least a portion of the lock therebetween when the lock is rotated between the prongs.

7. The interbody spacer system of claim 1 wherein the lock further includes a distal stop extending radially outwardly from the longitudinal axis and configured to abut the retainer to prevent movement of the lock out of the lock aperture.

8. The interbody spacer system of claim 1 wherein the cage further includes a lock recess defined by the sidewall being recessed; the main body being located within the lock recess and the main body residing above the sidewall in the lock recess.

9. The interbody spacer system of claim 8 wherein the lock recess intersects with at least one adjacent bone screw aperture.

10. The interbody spacer system of claim 1 wherein the lock is located between two bone screw apertures and the main body is configured to cover two adjacent bone screw heads.

11. The interbody spacer system of claim 1 wherein the main body of the lock includes two sides that are curved inwardly to create two concave sides.

12. The interbody spacer system of claim 1 wherein the lock-receiving location includes two oppositely disposed, parallel, flat lock-engaging surfaces configured to engage the at least two oppositely disposed flat surfaces of the post.

13. The interbody spacer system of claim 1 wherein the post has a cross-section taken perpendicular to the longitudinal axis of the lock; the cross-section having a length and a width; the length being longer than the width; wherein rotation of the lock imparts a cam-like motion with respect to the retainer.

14. The interbody spacer system of claim 1 wherein rotation of the lock imparts a cam-like motion with respect to the retainer.

* * * * *